US012685620B2

(12) United States Patent
Moshe et al.

(10) Patent No.: US 12,685,620 B2
(45) Date of Patent: Jul. 21, 2026

(54) IMAGE-BASED LONGITUDINAL ANALYSIS

(71) Applicant: Align Technology, Inc., San Jose, CA (US)

(72) Inventors: Maayan Moshe, Ramat HaSharon (IL); Ofer Saphier, Rehovot (IL); Shai Ayal, Shoham (IL); Michael Lellouch, Tel Aviv (IL); Ran Katz, Hod Hasharon (IL)

(73) Assignee: Align Technology, Inc., San Jose, CA (US)

( * ) Notice: Subject to any disclaimer, the term of this patent is extended or adjusted under 35 U.S.C. 154(b) by 53 days.

(21) Appl. No.: 18/801,609

(22) Filed: Aug. 12, 2024

(65) Prior Publication Data

US 2025/0049543 A1      Feb. 13, 2025

Related U.S. Application Data

(60) Provisional application No. 63/566,208, filed on Mar. 15, 2024, provisional application No. 63/519,222, filed on Aug. 11, 2023.

(51) Int. Cl.
*A61C 9/00* (2006.01)
*A61B 5/00* (2006.01)

(52) U.S. Cl.
CPC .......... *A61C 9/0053* (2013.01); *A61B 5/0088* (2013.01)

(58) Field of Classification Search
CPC ..... A61C 9/0053; A61C 9/004; A61B 5/0088; G16H 30/40
See application file for complete search history.

(56) References Cited

U.S. PATENT DOCUMENTS

| | | | |
|---|---|---|---|
| 6,099,314 | A | 8/2000 | Kopelman et al. |
| 6,334,772 | B1 | 1/2002 | Taub et al. |
| 6,334,853 | B1 | 1/2002 | Kopelman et al. |
| 6,463,344 | B1 | 10/2002 | Pavlovskaia et al. |
| 6,542,249 | B1 | 4/2003 | Kofman et al. |
| 6,633,789 | B1 | 10/2003 | Nikolskiy et al. |
| 6,664,986 | B1 | 12/2003 | Kopelman et al. |
| 6,697,164 | B1 | 2/2004 | Babayoff et al. |
| 6,845,175 | B2 | 1/2005 | Kopelman et al. |
| 6,979,196 | B2 | 12/2005 | Nikolskiy et al. |
| 7,030,383 | B2 | 4/2006 | Babayoff et al. |
| 7,202,466 | B2 | 4/2007 | Babayoff et al. |
| 7,255,558 | B2 | 8/2007 | Babayoff et al. |
| 7,286,954 | B2 | 10/2007 | Kopelman et al. |
| 7,319,529 | B2 | 1/2008 | Babayoff |

(Continued)

FOREIGN PATENT DOCUMENTS

EP          4210317 A1      7/2023

*Primary Examiner* — Haixia Du
(74) *Attorney, Agent, or Firm* — Shay Glenn LLP

(57) ABSTRACT

Methods and apparatuses (including devices and systems, such as intraoral scanners and software) for analyzing images of a subject's teeth. In some examples these methods may include examining the same teeth or tooth regions across different times and/or different imaging modalities, including but not limited to visible light, infrared, florescent, etc. Also described herein are methods and apparatuses for using a single, master, control for automatically or semi-automatically simultaneously adjusting multiple imaging parameters across multiple images of a region taken with different imaging modalities and/or at different times.

23 Claims, 15 Drawing Sheets

(56) References Cited

U.S. PATENT DOCUMENTS

| | | | |
|---|---|---|---|
| 7,373,286 B2 | 5/2008 | Nikolskiy et al. | |
| 7,507,088 B2 | 3/2009 | Taub et al. | |
| 7,545,372 B2 | 6/2009 | Kopelman et al. | |
| 7,698,068 B2 | 4/2010 | Babayoff | |
| 7,916,911 B2 | 3/2011 | Kaza et al. | |
| 8,108,189 B2 | 1/2012 | Chelnokov et al. | |
| 8,244,028 B2 | 8/2012 | Kuo et al. | |
| 8,587,582 B2 | 11/2013 | Matov et al. | |
| 8,948,482 B2 | 2/2015 | Levin | |
| D742,518 S | 11/2015 | Barak et al. | |
| 9,192,305 B2 | 11/2015 | Levin | |
| 9,261,356 B2 | 2/2016 | Lampert et al. | |
| 9,261,358 B2 | 2/2016 | Atiya et al. | |
| 9,299,192 B2 | 3/2016 | Kopelman | |
| D760,901 S | 7/2016 | Barak et al. | |
| 9,393,087 B2 | 7/2016 | Moalem | |
| 9,408,679 B2 | 8/2016 | Kopelman | |
| 9,431,887 B2 | 8/2016 | Boltanski | |
| 9,439,568 B2 | 9/2016 | Atiya et al. | |
| 9,451,873 B1 | 9/2016 | Kopelman et al. | |
| D768,861 S | 10/2016 | Barak et al. | |
| D771,817 S | 11/2016 | Barak et al. | |
| 9,491,863 B2 | 11/2016 | Boltanski | |
| D774,193 S | 12/2016 | Makmel et al. | |
| 9,510,757 B2 | 12/2016 | Kopelman et al. | |
| 9,660,418 B2 | 5/2017 | Atiya et al. | |
| 9,668,829 B2 | 6/2017 | Kopelman | |
| 9,675,430 B2 | 6/2017 | Verker et al. | |
| 9,693,839 B2 | 7/2017 | Atiya et al. | |
| 9,717,402 B2 | 8/2017 | Lampert et al. | |
| 9,724,177 B2 | 8/2017 | Levin | |
| 9,844,426 B2 | 12/2017 | Atiya et al. | |
| 10,076,389 B2 | 9/2018 | Wu et al. | |
| 10,098,714 B2 | 10/2018 | Kuo | |
| 10,108,269 B2 | 10/2018 | Sabina et al. | |
| 10,111,581 B2 | 10/2018 | Makmel | |
| 10,111,714 B2 | 10/2018 | Kopelman et al. | |
| 10,123,706 B2 | 11/2018 | Elbaz et al. | |
| 10,136,972 B2 | 11/2018 | Sabina et al. | |
| 10,390,913 B2 | 8/2019 | Sabina et al. | |
| 10,453,269 B2 | 10/2019 | Furst | |
| 10,456,043 B2 | 10/2019 | Atiya et al. | |
| 10,499,793 B2 | 12/2019 | Ozerov et al. | |
| 10,504,386 B2 | 12/2019 | Levin et al. | |
| 10,517,482 B2 | 12/2019 | Sato et al. | |
| 10,708,574 B2 | 7/2020 | Furst et al. | |
| 10,772,506 B2 | 9/2020 | Atiya et al. | |
| 10,888,399 B2 | 1/2021 | Kopelman et al. | |
| 10,952,816 B2 | 3/2021 | Kopelman | |
| 10,980,613 B2 | 4/2021 | Shanjani et al. | |
| D925,739 S | 7/2021 | Shalev et al. | |
| 11,238,586 B2 | 2/2022 | Minchenkov et al. | |
| 11,367,192 B2 | 6/2022 | Kopelman et al. | |
| 11,455,727 B2 | 9/2022 | Minchenkov et al. | |
| 11,478,132 B2 | 10/2022 | Kopelman et al. | |
| 11,563,929 B2 | 1/2023 | Saphier et al. | |
| 11,633,268 B2 | 4/2023 | Moalem et al. | |
| 11,707,238 B2 | 7/2023 | Moshe et al. | |
| RE49,605 E | 8/2023 | Kopelman | |
| 11,759,277 B2 | 9/2023 | Shalev et al. | |
| 11,806,210 B2 | 11/2023 | Moalem | |
| 11,896,461 B2 | 2/2024 | Saphier et al. | |
| 11,937,996 B2 | 3/2024 | Peleg | |
| D1,026,227 S | 5/2024 | Ginzburg et al. | |
| 11,995,839 B2 | 5/2024 | Weiss et al. | |
| 12,033,742 B2 | 7/2024 | Farkash et al. | |
| 12,042,124 B2 | 7/2024 | Rudnitsky et al. | |
| 12,076,200 B2 | 9/2024 | Saphier et al. | |
| 12,127,814 B2 | 10/2024 | Elbaz et al. | |
| 12,144,661 B2 | 11/2024 | Saphier et al. | |
| D1,061,895 S | 2/2025 | Ginzburg et al. | |
| 2017/0340418 A1 | 11/2017 | Raanan | |
| 2019/0231490 A1* | 8/2019 | Sabina | A61B 6/512 |
| 2020/0170760 A1 | 6/2020 | Dawood | |
| 2021/0321872 A1 | 10/2021 | Saphier et al. | |
| 2022/0233078 A1 | 7/2022 | Fridman et al. | |
| 2022/0323190 A1 | 10/2022 | Kopelman et al. | |
| 2022/0338723 A1 | 10/2022 | Farkash et al. | |
| 2022/0369910 A1 | 11/2022 | Gorfinkel et al. | |
| 2023/0021695 A1 | 1/2023 | Atiya et al. | |
| 2023/0025243 A1 | 1/2023 | Atiya et al. | |
| 2023/0042643 A1 | 2/2023 | Saphier et al. | |
| 2023/0068727 A1 | 3/2023 | Saphier et al. | |
| 2023/0309800 A1 | 10/2023 | Farkash et al. | |
| 2023/0346514 A1 | 11/2023 | Coslovsky et al. | |
| 2023/0380942 A1 | 11/2023 | Fain et al. | |
| 2023/0414331 A1 | 12/2023 | Saphier | |
| 2024/0008731 A1 | 1/2024 | Meyer et al. | |
| 2024/0024076 A1 | 1/2024 | Fridman | |
| 2024/0033057 A1 | 2/2024 | Saphier et al. | |
| 2024/0036448 A1 | 2/2024 | Atiya et al. | |
| 2024/0054729 A1* | 2/2024 | Stoustrup | G06T 15/005 |
| 2024/0115196 A1 | 4/2024 | Moshe et al. | |
| 2024/0122446 A1 | 4/2024 | Fridman et al. | |
| 2024/0164624 A1 | 5/2024 | Shalev et al. | |
| 2024/0197448 A1 | 6/2024 | Saphier et al. | |
| 2024/0202921 A1 | 6/2024 | Alkabetz et al. | |
| 2024/0245495 A1 | 7/2024 | Moalem et al. | |
| 2024/0285379 A1 | 8/2024 | Saphier et al. | |

* cited by examiner

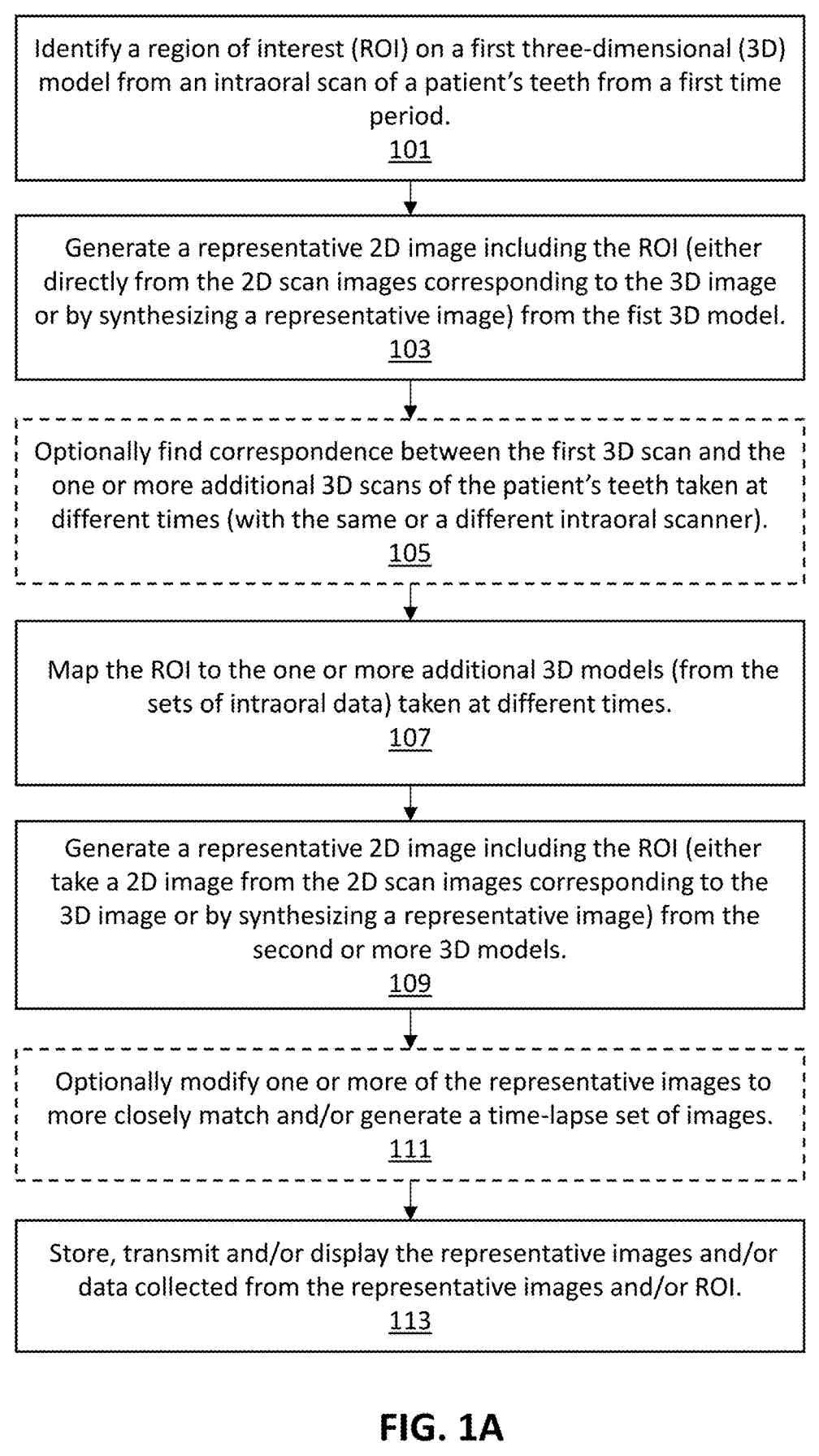

Identify a region of interest (ROI) on a first three-dimensional (3D) model from an intraoral scan of a patient's teeth from a first time period.
101

Generate a representative 2D image including the ROI (either directly from the 2D scan images corresponding to the 3D image or by synthesizing a representative image) from the fist 3D model.
103

Optionally find correspondence between the first 3D scan and the one or more additional 3D scans of the patient's teeth taken at different times (with the same or a different intraoral scanner).
105

Map the ROI to the one or more additional 3D models (from the sets of intraoral data) taken at different times.
107

Generate a representative 2D image including the ROI (either take a 2D image from the 2D scan images corresponding to the 3D image or by synthesizing a representative image) from the second or more 3D models.
109

Optionally modify one or more of the representative images to more closely match and/or generate a time-lapse set of images.
111

Store, transmit and/or display the representative images and/or data collected from the representative images and/or ROI.
113

FIG. 1A

Figure 1B:
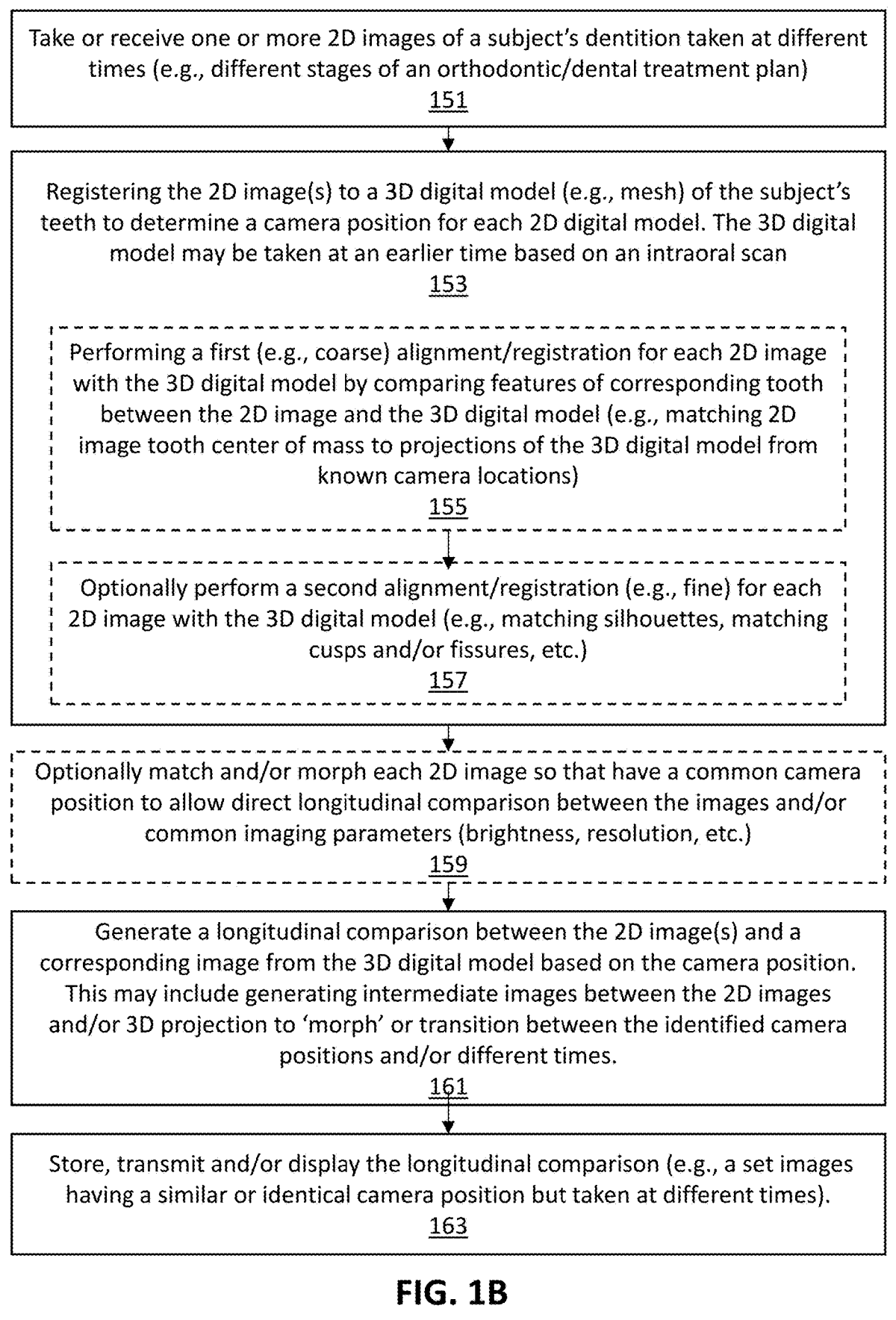

Take or receive one or more 2D images of a subject's dentition taken at different times (e.g., different stages of an orthodontic/dental treatment plan)
151

Registering the 2D image(s) to a 3D digital model (e.g., mesh) of the subject's teeth to determine a camera position for each 2D digital model. The 3D digital model may be taken at an earlier time based on an intraoral scan
153

Performing a first (e.g., coarse) alignment/registration for each 2D image with the 3D digital model by comparing features of corresponding tooth between the 2D image and the 3D digital model (e.g., matching 2D image tooth center of mass to projections of the 3D digital model from known camera locations)
155

Optionally perform a second alignment/registration (e.g., fine) for each 2D image with the 3D digital model (e.g., matching silhouettes, matching cusps and/or fissures, etc.)
157

Optionally match and/or morph each 2D image so that have a common camera position to allow direct longitudinal comparison between the images and/or common imaging parameters (brightness, resolution, etc.)
159

Generate a longitudinal comparison between the 2D image(s) and a corresponding image from the 3D digital model based on the camera position. This may include generating intermediate images between the 2D images and/or 3D projection to 'morph' or transition between the identified camera positions and/or different times.
161

Store, transmit and/or display the longitudinal comparison (e.g., a set images having a similar or identical camera position but taken at different times).
163

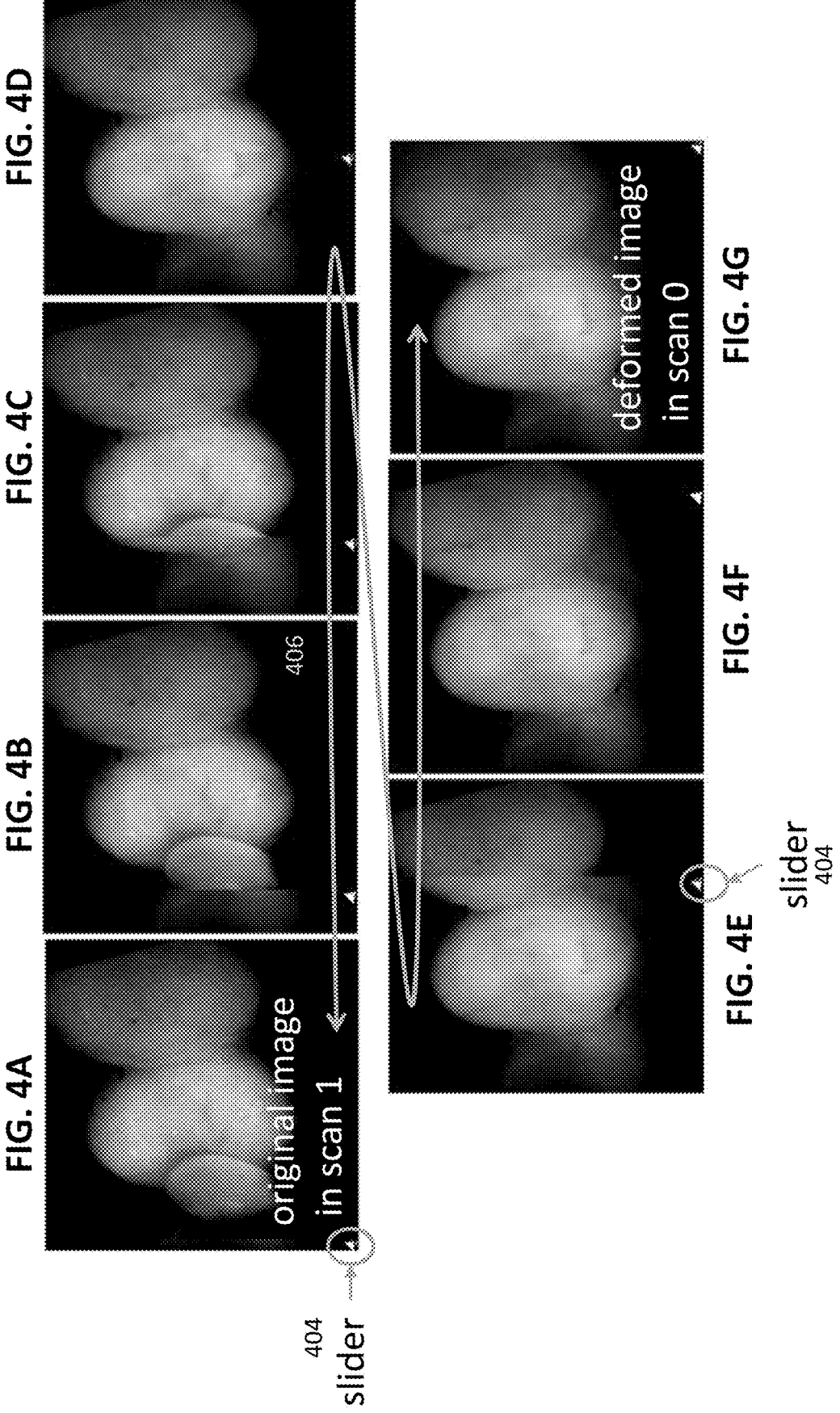

600

Scanner wand
602

Intraoral scanner                604

Processor                606

Memory                608

Control Logic                612

Display subsystem        614

User interface  Control
616

Display
618

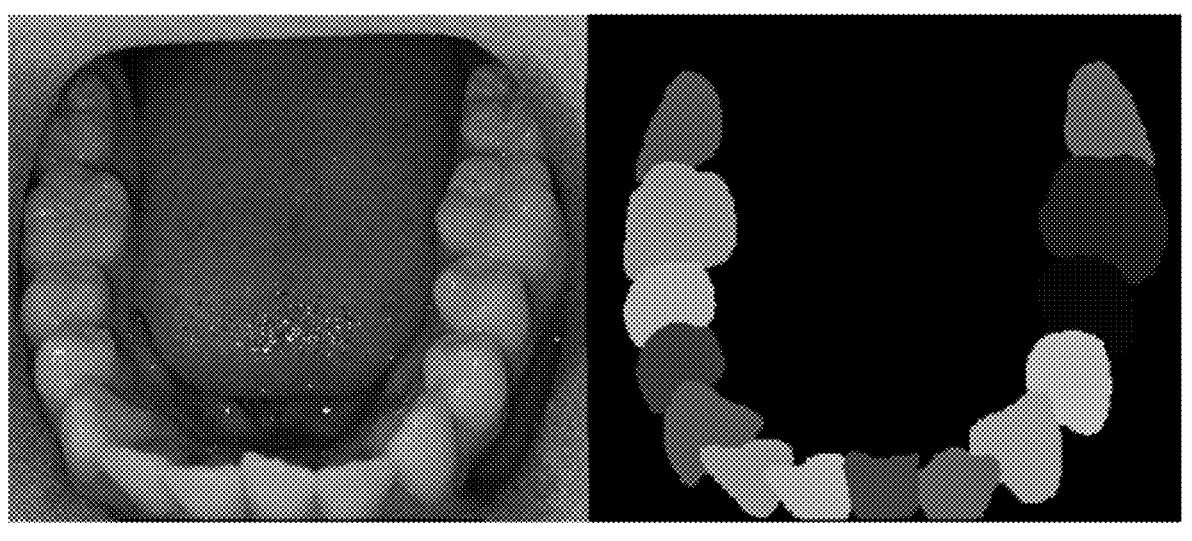
FIG. 7A                    FIG. 7B
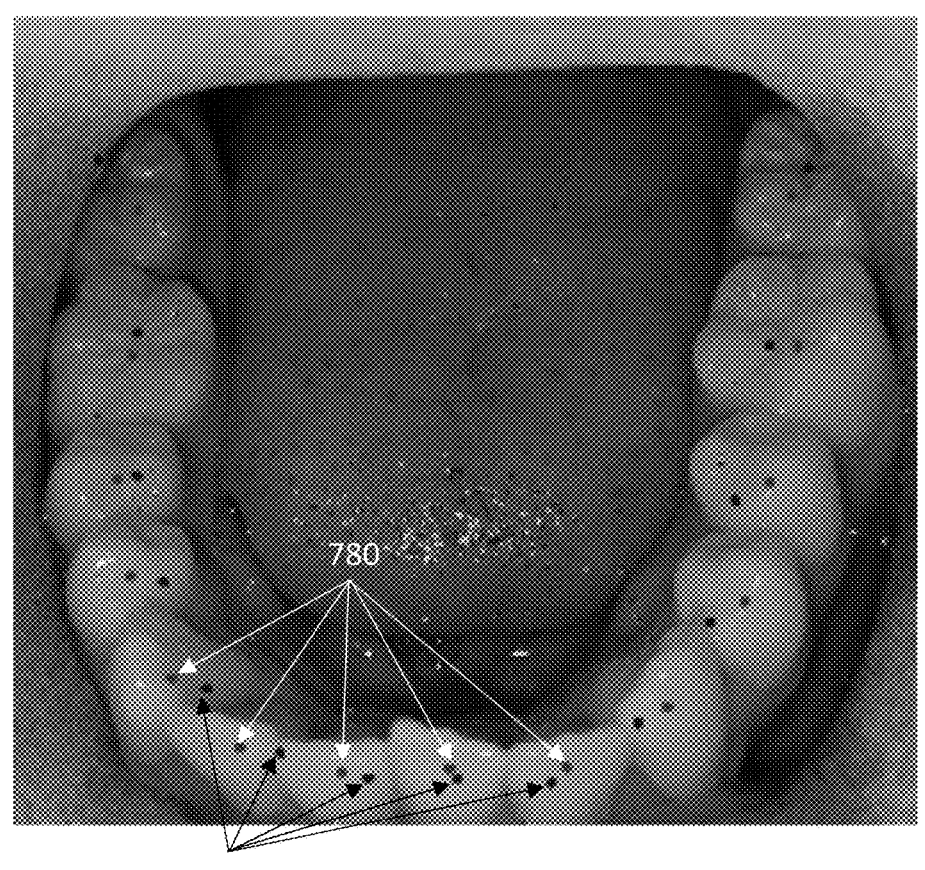
FIG. 7C

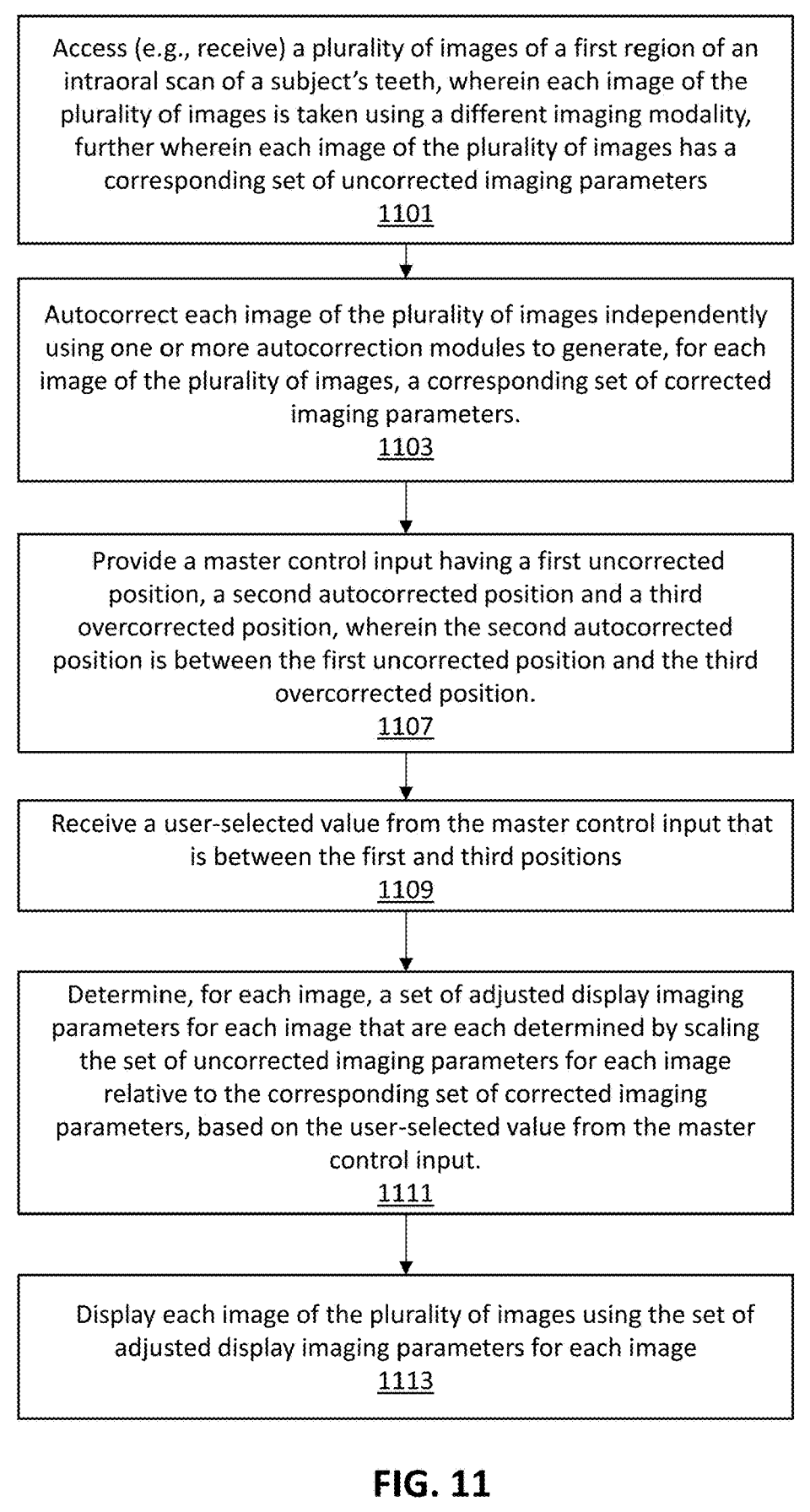

Access (e.g., receive) a plurality of images of a first region of an intraoral scan of a subject's teeth, wherein each image of the plurality of images is taken using a different imaging modality, further wherein each image of the plurality of images has a corresponding set of uncorrected imaging parameters
1101

Autocorrect each image of the plurality of images independently using one or more autocorrection modules to generate, for each image of the plurality of images, a corresponding set of corrected imaging parameters.
1103

Provide a master control input having a first uncorrected position, a second autocorrected position and a third overcorrected position, wherein the second autocorrected position is between the first uncorrected position and the third overcorrected position.
1107

Receive a user-selected value from the master control input that is between the first and third positions
1109

Determine, for each image, a set of adjusted display imaging parameters for each image that are each determined by scaling the set of uncorrected imaging parameters for each image relative to the corresponding set of corrected imaging parameters, based on the user-selected value from the master control input.
1111

Display each image of the plurality of images using the set of adjusted display imaging parameters for each image
1113

FIG. 11

IMAGE-BASED LONGITUDINAL ANALYSIS

CLAIM OF PRIORITY

This patent application claims priority to U.S. Provisional Patent Application No. 63/519,222, titled "IMAGE BASED LONGITUDINAL ANALYSIS," filed on Aug. 11, 2023, and to U.S. Provisional Patent Application No. 63/566,208, titled "APPARATUSES AND METHODS FOR ANALYSIS OF INTRAORAL SCANS," and filed on Mar. 15, 2024, each of which is herein incorporated by reference in its entirety.

BACKGROUND

Many dental and orthodontic procedures can benefit from accurate imaging (both 2D and 3D) of a subject's (e.g., patient's) dentition and intraoral cavity. It would be helpful to provide accurate visual descriptions of one or more regions of the teeth taken at different times to improve diagnostics and/or treatment of teeth. In particular, it would be extremely useful to provide descriptions of surface, and in some cases internal structures, of the teeth, including the enamel and dentin, as well as caries and structures that may be present on the teeth, such as dental appliances, fillings, pontics, and the like over time, including over the course of a treatment.

In recent years, dental imaging using intraoral scanning has become increasingly popular, and has resulted in patient records that may provide highly detailed descriptions of the patient's teeth at a particular point in time. However, even when the same intraoral scanner, or the same type of intraoral scanner, is used to take images of the patient's teeth at later times, it may be difficult or impossible to provide longitudinal images of the exact same regions of the teeth. For example, it has proven very difficult to generate accurate and smooth time-lapse images/videos, using patient scans taken with an intraoral scanner, because the intraoral scanner may be held in a user's hand, and may take numerous images at different positions, e.g., distances and angles, relative to the patient's teeth, and it is virtually impossible to show the same view in the same orientation. This makes it very difficult to make proper comparisons, particularly when comparing two-dimensional (2D) images. Existing techniques for generating time-lapse images or representations are algorithmically and computationally intensive.

In addition, it would be useful to provide longitudinal comparisons (e.g., comparisons over time) between two or more 2D images and/or between one or more 2D images and a 3D model, which may be taken at a different time.

Thus, it would be beneficial to provide methods and apparatuses to provide direct comparisons between corresponding regions of the subject's tooth or teeth across time (e.g., longitudinally), in a time-efficient and cost-effective manner. Described herein are methods and apparatuses that may address these issues.

SUMMARY OF THE DISCLOSURE

Described herein are methods and apparatuses (including devices and systems, such as intraoral scanners and software) for comparing images of the same teeth or tooth regions, and in some examples across different times. These methods and apparatuses may be used to compare between any one or more imaging type, including but not limited to visible light, infrared, florescent, etc. Comparison of the same teeth or regions of the teeth at different times may be referred to as longitudinal analysis. In general, longitudinal follow-up is an important part of the dental practice. These methods and apparatuses allow for easy comparisons of tooth images taken at different points in time. The images may be visible light images to show the surface of the teeth or near infra-red (NIR) images which penetrate the enamel and can show carious lesions. Since lesions can be detected in NIR even at early stages, the disclosed invention allows close follow up of early stage lesions. Thus, the methods and apparatuses described herein allow comparison of images for the same regions in the jaw over time. In some cases, once a Region of Interest (ROI) in the jaw is chosen (manually or automatically), these methods and apparatuses may choose the best images showing this ROI from each time. The images can be transformed to seem as if they are taken from the same camera position. For example, the images also may be straightened, and perspective corrected to have the ROI in the same orientation/perspective in all images allowing for simple comparison. The images being compared may be a comparison between 3D scan images (e.g., from an intraoral scanner), e.g., between different intraoral scans taken at different times, or they may be a comparison between one or more 2D image (taken with a camera, including patient cameras, such as smartphones) and one or more 3D intraoral scan, and/or may be comparisons between two or more 2D images (taken with a camera, including patient cameras, such as smartphones) taken at different times, which may use an intraoral scan as a reference for the comparison. The use of intraoral scans may computationally simplify the analysis of 2D images and may allow more rapid and accurate comparison as well as longitudinal analysis (e.g., analysis over time), including generating time-lapse images/videos which may require the accurate synthesis of intermediate images.

There are a number of technical problems associated with this longitudinal analysis of a patient's teeth, e.g., comparing across a patient's teeth at different times (days, months or even years apart), such as including finding the appropriate regions of the teeth to compare at different times (in some cases matching teeth), generating sufficiently similar views from these different times, and reducing the amount of computational time and resources (e.g., processing steps) needed for these steps. The methods and apparatuses described herein may solve these problems, and provide accurate and rapid comparison of the same teeth or tooth regions across different times periods from multiple intraoral scans, even when the scans were taken with different intraoral scanners, at different times and with different parameters. For example, these methods and apparatuses may include generating one or more synthetic two-dimensional (2D) images from each of the different sets of intraoral scans, and/or solving for an alignment transformation between different three-dimensional (3D) models, and/or using both 2D and 3D information to streamline the longitudinal comparisons.

In general, the methods and apparatuses described herein may use images and/or one or more sets intraoral scanning data taken at different times, in which each set of intraoral scanning data may include both a 3D digital model of the patient's teeth as well as a related series of 2D images for which a camera position is known (or directly derived). As mentioned, the different set of intraoral scanning data may be taken with different parameters, including different sensitivities (e.g., different light intensities, gain, etc.), different sizes of images, different (but overlapping) scanning regions of the teeth, and/or different relative positions from the teeth when the scan was taken, etc. In some cases at least two different sets of intraoral scanning data may be compared as described herein; any number of different sets of intraoral scanning data may be used and compared as described herein (e.g., three, four, five, six, seven, eight, nine, ten, etc.). In some cases two or more 2D images taken with a different camera, including a patient operated camera, such as a phone camera, may be used.

Each set of intraoral scan data may be associated with a particular time (e.g., a period or region of time during which the intraoral scan was taken). For example a first scan may be associated with a particular date, while a second (or more) intraoral scan data may be associated with a second date. The relative time difference may be known, e.g., the number of days, months, etc.) between each set of scan data, or just the sequence of the scan data may be known, e.g., first intraoral scan, second, etc. The time differences between these different sets of data may be the same or approximately the same (e.g., 2-5 days, 5-10 days, 10-15 days, 15-30 days, 1-2 months, 2-4 months, 4-6 months, 6-8 months, 9-10 months, 10-12 months, 1-2 years, 2-4 years, etc.), or they may be different.

Each set of intraoral scan data may include a plurality of two-dimensional scan images generated by the intraoral scanner. The intraoral scan data may include 2D scan images, including one or more of: visible light images (e.g., RGB images, white light images, individual wavelength images, etc.), near-IR light images, florescent images, or some combination of these. Each set of intraoral scan data may also include camera positional information associated with each 2D image. This positional information may reflect the relative position of the scanner (e.g., the tip, wand, etc. used to collect the image(s)) and may be a part each image, or may be included with the images (e.g., in an index), or both.

Optionally, each set of intraoral scan data may include a 3D model of the teeth (or jaw) generated from all or some of the 2D images. In some cases the 3D model may be a surface model of the teeth; alternatively or additionally the 3D model may include internal structures (e.g., may be a volumetric model). The 3D model(s) may be part of the set of intraoral scan data for each time period, or the 3D model(s) associated with each set of intraoral scan data may be generated as part of the methods described herein.

In general, the methods (and apparatuses for performing them) described herein may automatically or semi-automatically match fields of view between the different sets of intraoral scan data and/or 2D images. In some cases, matching may be performed by finding points defining a region of interest ("ROI") on one jaw of the scan. The ROI may be manually identified, via a user interface that allows or guides the user in determining the ROI on the 3D model corresponding to one of the intraoral scan data sets. In some examples the ROI may be automatically or semi-automatically determined, e.g., by detecting one or more features (e.g., carries, cracks, etc.), or regions having a high degree of change between the different 3D models, or the like. Once the ROI is determined on one of the 3D models a corresponding region may be identified on the other (one or more) 3D models. This step (or series of steps) may be performed by finding the correspondence between the 3D jaw scans, and using the correspondence, finding the points defining the ROI on the other jaws. For each jaw and points defining the ROI on that jaw a best representative two-dimensional (2D) image may be selected or identified, e.g., by finding an image that includes the most ROI points corresponding to the ROI in the 3D image for that intraoral scan data set, and/or the image taken from a position in which the camera angle is approximately normal to the surface containing the ROI in the 3D model, and/or an image that is closest to images of the ROI at different times. As described in greater detail herein, in some cases the representative images may be synthetized from the plurality of images of the intraoral scan data. In some cases a trained machine learning agent may generate the synthetic image(s), for example, a neural network may be trained go generate synthetic images from a desired camera position by rendering texture mapping from multiple images and taking into account the camera position at the time of image capturing. Once the representative set of images including the ROI for each of the different times is identified, the images may be further corrected (perspective correction, rotation, color equalization) to be as similar to each other as possible. The representative images may then be output (stored, transmitted and/or displayed). For example, the set of representative images may be presented using a graphical user interface (GUI) to allow easy comparison.

In general, the methods and apparatuses described herein may use the 3D surface scan of the jaw just to find the best matching images from the 2D scan(s); the comparisons of the corresponding ROIs may be done on the representative 2D images. In any of these examples, machine learning may be used to identify matching ROIs (e.g., matching fields of view) between the different 3D models. For example, matching fields of view of the images may be identified with neural radiance fields ("Nerf"). One more other methods for producing matching field of view images may be used, such as (but not limited to) light field fusion ("LLFF").

The methods described herein may be combined with other techniques for identifying one or more dental conditions, including but not limited to: caries, cracks, plaque, discoloration, malocclusion, gum swelling, tooth wear, tooth crowding, gum recession, etc. For example, any of these methods and apparatuses may use a severity map identifying one or more of these conditions, and using an identified region having a severity above a threshold value to determine a ROI on the 3D model automatically or semi-automatically. Thus, with the aid of a caries detection severity map these methods may allow the comparison of the severities of caries over time, e.g., either by comparing the area of the lesion, by confidence of the lesion or any other method.

In general, the representative images generated as descried herein for the different time periods may be compared in a user interface (GUI) that may include displaying these images either side-by-sides, or sequentially (e.g., as part of a loop, e.g., a video loop). In some examples synthetic images may be generated to represent times between these images. In some cases the representative images may be modified, e.g., by performing image processing to subtract, correlate, etc. these images relative to each other. In any of these methods and apparatuses, features corresponding to clinical features may be encoded. Features corresponding to clinical features may be encoded, and compared. For example, by encoding features of a clinical finding (e.g., by training an autoencoder) which may be invariant to camera position, encoded features may be compared. To account for changing findings, the data may be augmented with the same clinical finding from different times.

Any of these methods and apparatuses may be used with 3D models of the dentition, including but not limited to volumetric 3D models, which may be generated, for example, using near-IR data. Volumetric data (e.g., 3D volumetric models) may allow a comparison of lesion volumes directly (e.g., measuring the change in volume of carries over time, etc.). These methods and apparatuses may allow the comparison of images from multiplicity of sources including, but not limited to near-infrared (near IR), color images, x-ray images, etc. For example, any of these methods may include identifying the same field of view between different images and comparing severity maps, for example. By using severity maps (or any kind of invariant features) the methods described herein may compare severities from different capturing devices, including different intraoral scanners or the like.

For example, described herein are methods of generating a longitudinal series of intraoral images, the method comprising: identifying a region of interest (ROI) on a first three-dimensional (3D) model of a patient's teeth taken over a first time (wherein the scan is taken using an intraoral scanner); mapping the ROI in a plurality of images corresponding to the first 3D model; generating or selecting a first representative image that is two-dimensional (2D), wherein the first representative image includes a maximum number of points defining the ROI and/or has a corresponding camera angle that is approximately normal to a surface containing the ROI in the 3D model; generating a second representative image corresponding to a second 3D model, wherein the second representative image is 2D and corresponds to the same camera angle relative to the second 3D model as the first representative image and includes a region of the second 3D model that corresponds to the ROI; modifying the first and/or second representative images so that the first and second representative images match more closely to each other; and displaying the first and second representative images.

In some examples, a method of generating a longitudinal series of intraoral images may include: identifying a region of interest (ROI) (e.g., identifying a plurality of points defining the ROI) on a first three-dimensional (3D) model of a patient's teeth derived from a first intraoral scan taken over a first time period using an intraoral scanner; finding correspondence between the first 3D model and a second 3D model of the patient's teeth taken over a second time with the same or a different intraoral scanner; finding points corresponding to one or more of the plurality of points defining the ROI in each of a plurality of images corresponding to the first 3D model, and generating a first representative image that is two-dimensional (2D), wherein the first representative image includes a maximum of the plurality of points defining the ROI and/or has a corresponding camera angle that is approximately normal to a surface containing the ROI in the 3D model; generating a second representative image corresponding to the second 3D model, wherein the second representative image has to the same camera angle as the first representative image relative to the second 3D model as the first representative image and includes a region of the second 3D model that corresponds to the ROI; modifying the first and/or second representative images to adjust one or more of: perspective, rotation or color equalization so that the first and second representative images match more closely to each other; and displaying the first and second representative images.

In general, identifying the ROI may include using a trained neural network to select the ROI, wherein the trained neural network is trained to identify one or more clinical features from the 3D model or a plurality of 2D images corresponding to the 3D model. In some examples, identifying the ROI comprises receiving the ROI from a user.

Any of these methods may include finding correspondence between the first 3D model and the second 3D model of the patient's teeth taken over the second time, before generating the second representative image.

The second 3D model may be taken with a different intraoral scanner than the first 3D model, or in some examples with the same (or the same model of) intraoral scanner as the first 3D model.

Mapping the ROI in the plurality of images corresponding to the first 3D model may include identifying points corresponding to one or more of a plurality of points defining the ROI in each of a plurality of images corresponding to the first 3D model, further wherein generating or selecting the first representative 2D image comprises selecting the first representative 2D image from the first plurality of images corresponding to the first 3D model. For example, mapping the ROI in the plurality of images corresponding to the first 3D model may include identifying points corresponding to one or more of a plurality of points defining the ROI in each of a plurality of images corresponding to the first 3D model, further wherein generating or selecting the first representative 2D image comprises generating a synthetic image from the first 3D model and/or the plurality of images corresponding to the first 3D model. The synthetic image may have a camera angle that is approximately normal to a surface containing the ROI in the 3D model.

Any of these methods may include identifying, in a plurality of images corresponding to the second 3D model, points corresponding to one or more of a plurality of points defining the ROI in the first 3D model.

Generating the second representative image corresponding to the second 3D model may include generating a synthetic images taken using the same camera angle relative to the second 3D model as the first representative image. Generating the synthetic image may include using a trained neural network to generate the synthetic image. Generating the synthetic image may further comprise textural mapping the synthetic image to make it photorealistic. In some examples generating the synthetic image further comprises generating the synthetic image by one or more of: light field fusion (LLFF), Neural Radiance Fields ("NERF"), or scene representation networks (SRN).

Modifying the first and/or second representative images may include adjusting one or more of: perspective, rotation or color equalization.

Displaying the first and second representative images may include displaying the first and second representative images side-by-side. In some cases displaying the first and second representative images comprises displaying the first and second representative images as part of a video loop.

Any of these methods may include comparing one or more regions of the first and second representative images and outputting data regarding the differences between the representative images. For example, comparing may include comparing a caries detection severity map for the first representative image to a caries detection severity map for the second representative image.

The first three-dimensional (3D) scan of the patient's teeth may include an infrared scan.

Also described herein are apparatuses configured to perform any of these methods, as well as systems for performing them, including (but not limited to) intraoral scanning systems configured to perform them. These apparatuses may include software configured to perform these methods. For example, described herein are non-transitory computer-readable medium comprising instructions which, when executed by one or more processors, causes the one or more processors to perform a method comprising: identifying a region of interest (ROI) on a first three-dimensional (3D) model of a patient's teeth taken over a first time (e.g., taken using an intraoral scanner); mapping the ROI in a plurality of images corresponding to the first 3D model; generating or selecting a first representative image that is two-dimensional (2D), wherein the first representative image includes a maximum number of points defining the ROI and/or has a corresponding camera angle that is approximately normal to a surface containing the ROI in the 3D model; generating a second representative image corresponding to a second 3D model, wherein the second representative image is 2D and corresponds to the same camera angle relative to the second 3D model as the first representative image and includes a region of the second 3D model that corresponds to the ROI; modifying the first and/or second representative images so that the first and second representative images match more closely to each other; and displaying the first and second representative images.

As used herein, a processor may include hardware that runs the computer program code. Specifically, the term 'processor' may include a controller and may encompass not only computers having different architectures such as single/multi-processor architectures and sequential (Von Neumann)/parallel architectures but also specialized circuits such as field-programmable gate arrays (FPGA), application specific circuits (ASIC), signal processing devices and other devices.

For example, a non-transitory computer-readable medium comprising instructions which, when executed by one or more processors, causes the one or more processors to perform a method comprising: identifying a region of interest (ROI) (e.g., identifying a plurality of points defining the ROI) on a first three-dimensional (3D) model of a patient's teeth derived from a first intraoral scan taken over a first time period using an intraoral scanner; finding correspondence between the first 3D model and a second 3D model of the patient's teeth taken over a second time with the same or a different intraoral scanner; finding points corresponding to one or more of the plurality of points defining the ROI in each of a plurality of images corresponding to the first 3D model, and generating a first representative image that is two-dimensional (2D), wherein the first representative image includes a maximum of the plurality of points defining the ROI and/or has a corresponding camera angle that is approximately normal to a surface containing the ROI in the 3D model; generating a second representative image corresponding to the second 3D model, wherein the second representative image has to the same camera angle as the first representative image relative to the second 3D model as the first representative image and includes a region of the second 3D model that corresponds to the ROI; modifying the first and/or second representative images to adjust one or more of: perspective, rotation or color equalization so that the first and second representative images match more closely to each other; and displaying the first and second representative images.

An intraoral scanning apparatus as described herein may be configured to display a longitudinal series of intraoral images. For example, an intraoral scanning apparatus may include: an intraoral scanning wand; one or more processors; and the non-transitory computer-readable medium as described herein.

For example, described herein are intraoral scanning systems comprising: a hand-held imaging sensor; and a non-transitory, computer-readable storage medium comprising instructions which, when executed by a computer, cause the computer to carry out the steps of: identifying a region of interest (ROI) on a first three-dimensional (3D) model of a patient's teeth derived from a first intraoral scan taken over a first time period; generating or selecting a first representative image that is two-dimensional (2D) and that includes the ROI from a plurality of 2D images corresponding to the first intraoral scan (for example, generating or selecting may be based on the number of points defining the ROI and/or a camera angle relative to a surface of the 3D model containing the ROI); mapping the ROI from the first 3D model to a second 3D model of a second set of intraoral scan data; generating a second 2D representative image corresponding to the second 3D model, wherein the second representative image corresponds to the same camera angle relative to the second 3D model as the first representative image relative to the first 3D model and includes a region of the second 3D model that corresponds to the ROI; and displaying the first and second representative images.

In any of these methods and apparatuses, generating or selecting the first representative image may comprise selecting the first representative image from a plurality of images, and further wherein the selection is based on the number of points defining the ROI and/or a camera angle relative to a surface containing the ROI. For example, generating the synthetic image may include using an angle normal to a surface containing the ROI in the first 3D model to determine a camera angle of the synthetic image. In some examples the camera angle may be set to the angle normal to the surface containing the ROI or may be approximately normal (e.g., within +/−2 degrees, 5 degrees, 7.5 degrees, 10 degrees, 15 degrees, etc.).

For example, an intraoral scanning system may include: a hand-held imaging sensor; and a non-transitory, computer-readable storage medium comprising instructions which, when executed by a computer, cause the computer to carry out the steps of: identifying a plurality of points defining a region of interest (ROI) on a first three-dimensional (3D) model of a patient's teeth taken over a first time; finding correspondence between the first 3D model and a second 3D model of the patient's teeth taken over a second time; finding points corresponding to one or more of the plurality of points defining the ROI in each of a plurality of images corresponding to the first 3D model, and generating a first representative image that is two-dimensional (2D), wherein the first representative image includes a maximum of the plurality of points defining the ROI and/or has a corresponding camera angle that is approximately normal to a surface containing the ROI in the 3D model; generating a second representative image corresponding to the second 3D model, wherein the second representative image has to the same camera angle as the first representative image relative to the second 3D model as the first representative image and includes a region of the second 3D model that corresponds to the ROI; modifying the first and/or second representative images to adjust one or more of: perspective, rotation or color equalization so that the first and second representative images match more closely to each other; and displaying the first and second representative images.

As a general matter the methods and apparatuses may refer to a "first 3D model" and "first" intraoral scan and/or "first" set of intraoral data, as well as and additional (including "second" or "third") 3D models and sets of intraoral data corresponding to them; it should be understood that the order of these models is not intended to correspond to their chronological time sequence. The first 3D model and corresponding scan/scan data may be the earliest in time, or it may be the lasted in time or it may be a scan from an intermediate time.

Also described herein are method for generating a longitudinal comparison (e.g., a set of images showing the change in dentition over time, which may be directed to the same region of the teeth). For example, a method may include: receiving or accessing one or more two-dimensional (2D) images of a subject's dentition taken at different times; registering each of the one or more 2D images to a three-dimensional (3D) digital model of the patient's teeth to determine a camera position for each of the one or more 2D images relative to the patient's teeth; generate a longitudinal comparison between the one or more 2D images relative to each other and/or to a projection taken from the 3D digital model using the identified camera positions; and outputting the longitudinal comparison.

In any of these method the one or more 2D images of the subject's dentition may be taken by the patient. The 2D images may be taken at different times and/or stage of a treatment plan, including an orthodontic and/or dental treatment plan. For example, the one or more 2D image of the subject's dentition may each taken at a different stage of a treatment plan.

Any of these methods may include preprocessing each of the one or more 2D images to segment the one or more 2D images to identify teeth and/or to remove non-tooth region of the image (e.g., setting the pixels to a neutral value).

The 3D digital model may be based on an intraoral scan taken at an earlier time than the one or more 2D images. In any of these examples, registering each of the one or more 2D images may comprise aligning each of the one or more 2D images by iteratively comparing each of the one or more 2D images to projections from the 3D digital model to minimize a difference between one or more features of the teeth. The one or more features may comprise a center of mass, a tooth height, width, silhouette, etc. Any of these methods may include performing a second registration between each of the one or more 2D images to the 3D digital model of the patient's teeth to improve the determined camera position for each of the one or more 2D images by iteratively comparing each of the one or more 2D images to projections from the 3D digital model to minimize a difference between a second feature of the teeth in the one or more 2D images and the projections from the 3D digital model.

In examples in which multiple 2D images taken at different times are used, the method or apparatus (e.g., system) for performing the methods may determine if the 2D images are within a reasonable camera position relative to each other so that longitudinal comparisons may be performed. The methods and apparatuses may identify a separate camera position for each of the 2D images, and may generate a common (e.g., consensus, average, intermediate, etc.) camera position for the set of 2D images. In some cases the method may morph or modify the 2D images to reflect the consensus camera position. For example, the method may include setting the identified camera position to an intermediate position between the identified camera positions from for each of the one or more 2D images. For example, any of these methods may include matching each of the one or more 2D images and the projection taken from the 3D digital model to a common (e.g., consensus) camera position based on the identified camera positions. Alternatively the method may generate one or more (e.g., a set or series) of images to morph the time series of 2D images to more smoothly transition between the 2D images taken at different times, which may form a part of the longitudinal comparison. Any of these methods may include a projected image from the 3D digital model as part of the longitudinal comparison. For example, any of these methods may include generating one or more virtual intermediate images (to be included as part of the longitudinal comparison) morphing the one or more 2D images and/or the projection of the 3D digital model at the identified camera position.

As mentioned, outputting may comprise displaying the longitudinal comparison and/or transmitting and/or storing the longitudinal comparison.

For example, a method may include: receiving or accessing one or more 2D images two-dimensional (2D) images of a subject's dentition taken at different times; registering each of the one or more 2D images to a three-dimensional (3D) digital model of the patient's teeth to determine a camera position for each of the 2D images relative to the patient's teeth by iteratively comparing each of the one or more 2D images to projections from the 3D digital model to minimize a difference between one or more features of the teeth; generate a longitudinal comparison between the one or more 2D images relative to each other and/or to a projection taken from the 3D digital model using the identified camera positions; match each of the one or more 2D images and the projection taken from the 3D digital model to have a common camera position based on the identified camera positions; outputting the longitudinal comparison.

Also described herein are methods and apparatuses for controlling the display of multiple images of the same region of the teeth in different modalities using simplified controls, including in some cases a "master" control to concurrently adjust multiple imaging/display parameters at different times.

Any of the apparatuses and methods described herein may provide comparison between multiple different images, including images of the same general region taken at different times and/or at different imaging modalities (e.g. visible light, near-infrared light, etc.) or both. Also described herein are methods and apparatuses, including user interfaces (and software for performing these methods and/or implementing these apparatuses) including tools for automatically or semi-automatically modifying the images in order to allow visualization in a manner that is not otherwise possible. These methods and apparatuses solve the technical problem of autocorrecting image parameters across images having different imaging modalities. Current techniques are inadequate, as they are not capable of concurrently optimizing imaging parameter of different images and different imaging modalities, instead introducing artifacts and requiring further manual correction. The technical solutions provided herein may include scaling In general, the methods and apparatuses described herein may include setting a plurality of autocorrect positions for a single master control input that is capable of optimally adjusting the plurality of different images, and in particular intraoral images.

For example, described herein are methods comprising: receiving or accessing a plurality of images of a first region of an intraoral scan of a subject's teeth, wherein each image of the plurality of images is taken using a different imaging modality, further wherein each image of the plurality of images has a corresponding set of uncorrected imaging parameters; autocorrecting each image of the plurality of images independently using one or more autocorrection modules to generate, for each image of the plurality of images, a corresponding set of corrected imaging parameters; providing a master control input having a first uncorrected position, a second autocorrected position and a third overcorrected position, wherein the second autocorrected position is between the first uncorrected position and the third overcorrected position; receiving a user-selected value from the master control input that is between the first and third positions; determining, for each image, a set of adjusted display imaging parameters for each image that are each determined by scaling the set of uncorrected imaging parameters for each image relative to the corresponding set of corrected imaging parameters, based on the user-selected value from the master control input; and displaying each image of the plurality of images using the set of adjusted display imaging parameters for each image.

Scaling the set of uncorrected imaging parameters for each image relative to the corresponding set of corrected imaging parameters may include offsetting the uncorrected imaging parameters for each image between 0% and 200% of a difference between the set of uncorrected imaging parameters for each image and the corresponding set of corrected imaging parameters, based on the user-selected value from the master control input.

The set of adjusted display imaging parameters for each image may be uncorrected from the set of uncorrected imaging parameters when the user-selected value from the master control input corresponds to the first, uncorrected, position. The set of adjusted display imaging parameters for each image may be set to the corresponding set of corrected imaging parameters when the user-selected value from the master control input corresponds to the second, autocorrected, position.

The plurality of uncorrected parameters may comprise any appropriate parameters, including contrast and brightness. The different imaging modalities may comprise two or more of: white light illumination, near-infrared illumination, single-wavelength illumination, and florescent illumination.

Any of these methods may include iteratively determining, for each image, the set of adjusted display imaging parameters and displaying each image of the plurality of images using the set of adjusted display imaging parameters in real time as the user adjusts the master control input.

Providing the master control input may comprise providing one or more of: a slider, a knob, or a dial. Receiving a user-selected value from the master control input may comprise receiving a continuous value.

Autocorrecting each image of the plurality of images using the one or more autocorrection modules may include one or more modules configured to perform one or more of: histogram equalization, gamma correction, color balance correction, white balance correction, sharpening filters, noise reduction, contrast stretching, saturation adjustment, and blur removal.

Any of these methods may include receiving a user-selected position relative to a three-dimensional (3D) model of the subject's teeth corresponding to the first region of the intraoral scan, wherein the 3D model of the subject's teeth is derived from the intraoral scan of the subject's teeth.

The plurality of images of a first region of an intraoral scan may comprise a first white-light image and a second near-infrared (NIR) image.

Any of these methods may include allowing the user to toggle between using the master control input and a plurality of individual control inputs corresponding to each of the imaging parameters for each image of the plurality of images.

Displaying each image of the plurality of images may comprise displaying each image side-by-side (right/left and/ or top/bottom). Alternatively, the images may be displayed overtop of each other (e.g., alternately displayed, which may highlight changes).

In any of these methods, the method may be performed by an intraoral scanner.

For example, a method may include: receiving or accessing a first image of a first region of an intraoral scan of a subject's teeth, wherein the first image is taken using a first imaging modality, the first image having first plurality of uncorrected imaging parameters; receiving or accessing a second image of the first region of the intraoral scan of the subject's teeth, wherein the second image is taken using a second imaging modality, the second image having second plurality of uncorrected imaging parameters; autocorrecting the first image using one or more autocorrection modules to generate a first set of corrected imaging parameters; autocorrecting the second image using the one or more autocorrection modules to generate a second set of corrected parameters; provide a master control input having a first uncorrected position, a second autocorrected position and a third overcorrected position, wherein the second autocorrected position is between the first uncorrected position and the third overcorrected position; receiving a user-selected value from the master control input that is between the first and third positions; displaying the first image using a first plurality of display imaging parameters that are determined by scaling the first plurality of uncorrected imaging parameters relative to the first set of corrected imaging parameters based on the user-selected value from the master control input; and displaying the second image using a second plurality of display imaging parameters that are determined by scaling the second plurality of uncorrected imaging parameters relative to the second set of corrected imaging parameters based on the user-selected value from the master control input.

Also described herein are systems including or configured to perform these techniques. For example, a system may include: one or more processors; a memory coupled to the one or more processors, the memory storing computer-program instructions, that, when executed by the one or more processors, perform a computer-implemented method comprising: receiving or accessing a plurality of images of a first region of an intraoral scan of a subject's teeth, wherein each image of the plurality of images is taken using a different imaging modality, further wherein each image of the plurality of images has a corresponding set of imaging parameters (which may be uncorrected or previously corrected); autocorrecting each image of the plurality of images independently using one or more autocorrection modules to generate, for each image of the plurality of images, a corresponding set of corrected imaging parameters; providing a master control input having a first uncorrected position, a second autocorrected position and a third overcorrected position, wherein the second autocorrected position is between the first uncorrected position and the third overcorrected position; receiving a user-selected value from the master control input that is between the first and third positions; determining, for each image, a set of adjusted display imaging parameters for each image that are each determined by scaling the set of uncorrected imaging parameters for each image relative to the corresponding set of corrected imaging parameters, based on the user-selected value from the master control input; and displaying each image of the plurality of images using the set of adjusted display imaging parameters for each image.

The system may be configured so that scaling the set of uncorrected imaging parameters for each image relative to the corresponding set of corrected imaging parameters may comprise offsetting the uncorrected imaging parameters for each image between 0% and 200% of a difference between the set of uncorrected imaging parameters for each image and the corresponding set of corrected imaging parameters, based on the user-selected value from the master control input. The set of adjusted display imaging parameters for each image may be uncorrected from the set of uncorrected imaging parameters when the user-selected value from the master control input corresponds to the first, uncorrected, position. The set of adjusted display imaging parameters for each image may be set to the corresponding set of corrected imaging parameters when the user-selected value from the master control input corresponds to the second, autocorrected, position. The plurality of uncorrected parameters may comprise contrast and/or brightness. The different imaging modalities may comprise two or more of: white light illumination, near-infrared illumination, single-wavelength illumination, and florescent illumination.

The processor may be further configured to iteratively determine, for each image, the set of adjusted display imaging parameters and displaying each image of the plurality of images using the set of adjusted display imaging parameters in real time as the user adjusts the master control input. Providing the master control input may comprise providing one or more of: a slider, a knob, or a dial. Receiving a user-selected value from the master control input may comprise receiving a continuous value. Autocorrecting each image of the plurality of images using the one or more autocorrection modules may comprise one or more modules configured to perform one or more of: histogram equalization, gamma correction, color balance correction, white balance correction, sharpening filters, noise reduction, contrast stretching, saturation adjustment, and blur removal.

The processor may be further configured to include receive a user-selected position relative to a three-dimensional (3D) model of the subject's teeth corresponding to the first region of the intraoral scan, wherein the 3D model of the subject's teeth is derived from the intraoral scan of the subject's teeth. The plurality of images of a first region of an intraoral scan may comprise a first white-light image and a second near-infrared (NIR) image. The processor may be further configured to allow the user to toggle between using the master control input and a plurality of individual control inputs corresponding to each of the imaging parameters for each image of the plurality of images. Displaying each image of the plurality of images may comprise displaying each image side-by-side.

In general, the system may be configured as (or may include) an intraoral scanner. For example, the processor(s) of the system may be part of the processors of the intraoral scanner (either local or remote to the scanner) and/or may be separate.

Also described herein are computer-readable storage media comprising instructions configured to perform any of these methods.

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIG. 1A schematically illustrates a method of generating a longitudinal series of intraoral images as described herein.

FIG. 1B schematically illustrates an example of a method of generating a longitudinal set of image as described herein.

FIG. 3A shows a first representative image from a first set of intraoral scan data ("scan 0") taken at a first time. FIG. 3B shows a second representative image from a second set of intraoral scan data ("scan 1") prior to post-processing to realign (e.g., resample) the image to better match the representative image form the first set of intraoral scan data. FIG. 3C shows the post-processed second representative image from the second set of intraoral scan data.

FIGS. 4A-4G illustrate one example of a method of displaying a set of representative images.

FIG. 7A-7B show an example of a 2D image of a subject's dentition and FIG. 7B shows preprocessed version of the image of FIG. 7A, in which non-tooth pixels have been modified (e.g., removed, masked, etc.) and the image has been segmented to identify individual teeth.

FIG. 7C shows a 2D image of FIG. 7A in which centers of mass of the segmented teeth from the 2D image are shown along with centers of mass from a projection of the 3D digital model of the patient's teeth are shown for comparison. The method may iteratively take 2D projection images from different (known) camera positions to determine a best match between the centers of mass that may best match in order to provide alignment of the 2D image with the 3D digital model.

FIG. 10B shows the identification of cusps and fissures in the 2D image which may be compared with projections of the 3D digital model for which cusps and fissures have been identified.

FIG. 11 illustrates one method of controlling imaging parameters concurrently across multiple images of an intraoral scan.

DETAILED DESCRIPTION

Figure 2A:
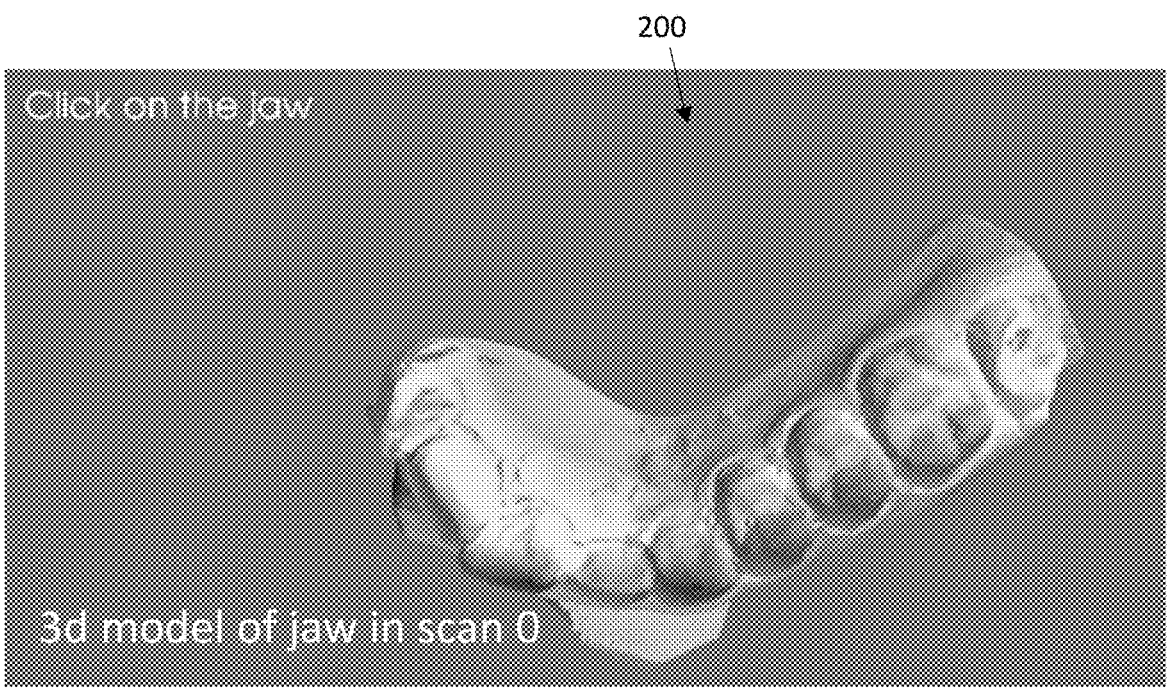
FIGS. 2A-2B illustrate one example of a user selecting a region of interest (ROI) using a graphical user interface.

Described herein are methods and apparatuses for generating accurate and clear images, including (but not limited to) time-lapse images/videos, using patient scans taken with an intraoral scanner and/or 2D images taken with a camera (such as a patient operated camera). In some cases the methods described herein may allow the selection of the region of interest (ROI) as a point or region from the 3D model using a user interface. For example, the user may manipulate a display of the 3D model of the teeth taken at a first time and may either select a region (direct selection) by dropping a marker onto a region. In some examples, the user may indirectly select the region by zooming in on a region or dwelling on a region. Another indirect selection may include automatically selecting a region from an approximate center of the displayed 3D model (e.g., 3D model representing the set of intraoral scan data).

Also described herein are methods and apparatuses for correcting (e.g., autocorrecting) images of one or more regions taken with different imaging modalities, including but not limited to visible light, near-infrared (near-IR), etc.

FIG. 1A schematically illustrates a first example of a method of generating a longitudinal series of intraoral images. As shown in FIG. 1A, the method, or an apparatus configured to perform the method, may first identify a region of interest (ROI) on a first 3D model of a patient's teeth. The first 3D model may be derived from a first set of intraoral scanning data that is taken at a first time 101 by an intraoral scanner. The first 3D model may be included as part of the set of intraoral scanning data, or it may be generated as part of the method described herein, e.g., from the series of intraoral scans of the first 3D model. Thus, in some examples the method may include generating, or modifying, the first 3D model of the patient's teeth. The 3D models of the patient's teeth described herein may be 3D models of a patient's dental arch (e.g., upper arch and/or lower arch). The upper and lower arches (e.g., upper and lower jaws) may be processed together, or may be processed separately.

In general, these methods may include receiving the sets of intraoral scanning data, e.g., from a database or as part of an intraoral scanner. The sets of intraoral scanning data may include the 3D model and the plurality of scan images used to generate the 3D model. The scans may include one or more scanning modality (e.g., visible light, near-IR light, florescent data, etc.). For example in some cases the set of intraoral scanning data may include multiple channels corresponding to intraoral scan data. The sets of intraoral scanning data may be stored in one or more local or remote databases and accessed as needed to perform the methods described herein.

The ROI may be determined manually, semi-automatically or automatically. For example, the ROI may be received from user input. In some examples the user may be presented with the 3D model in a user interface, and may manipulate the 3D model (e.g., rotate, translate, zoom in/zoom out, etc.) and may identify the ROI directly on the 3D model. For example, the user may mark (using a tool from the user interface) the ROI on the 3D model. Alternatively, in some examples the method or apparatus may suggest and ROI from the 3D model. In some cases the method or apparatus may propose an ROI based on one or more identified dental conditions (e.g., caries, cracks, etc.). In some case a severity map including one or more dental conditions (e.g., a caries detection severity map) may be used to determine an ROI including one or more dental conditions. The size of the ROI may be preset or user-adjusted (e.g., to include a predetermined region of the tooth or teeth).

In some cases an ROI may be automatically determined from the first 3D model by determining a region of the surface (and/or internal anatomy) of the 3D model including one or more dental conditions. In some variation the method may be semi-automatic by presenting one or more options for the ROI (e.g., marked on the 3D model) to the user and allowing the user to accept/reject and/or modifying the ROI (increasing/decreasing, translating, etc.) the position and/or size of the ROI. In some cases the user interface may present one or more ROIs specific to each of two or more different dental conditions, or may receive a selection from the user of which of one or more conditions to use to identify the ROI. For example, a user interface may include a menu of dental conditions and allow the user to select which dental condition(s) to use to select the ROI from the 3D model.

In general, the methods described herein may include using the ROI on the first 3D model to identify a first representative 2D image 103. The representative 2D image may be taken from the 2D scans of the first set of intraoral scanning data or it may be synthesized from the set of intraoral scanning data. The method may include finding points corresponding to one or more of the plurality of points defining the ROI (or an outline of the ROI) in each of a plurality of 2D images corresponding to the first 3D model, and generating a first 2D representative image, wherein the first representative image includes the maximum number of the points defining the ROI (or the outline of the ROI) and/or has a corresponding camera angle that is approximately normal to a surface containing the ROI in the 3D model.

Either before or after selecting the ROI from a first set of intraoral scanning data (e.g., identifying the ROI on a 3D model from the first set of intraoral scanning data), the method may include finding correspondence between the first 3D model and a second 3D model of the patient's teeth taken over a second time with the same or a different intraoral scanner 105. Each of the sets of intraoral scanning data taken from the same patient at different times may be analyzed by the method or system (e.g., automatically) to identify a correspondence relationship ("correspondence") between the 3D models. The correspondence relationship may allow approximate translation between the different 3D models for all of the sets of intraoral scanning data taken at different times, even as the patient's teeth are changing. A correspondence between multiple 3D models may identify relations (or mappings) between a plurality of landmark elements of the 3D models, including one or more teeth (e.g., based on tooth shape, etc.) or portions of one or more teeth (e.g., cusp(s), ridge(s), etc.). The landmark elements may be relatively invariant between the multiple different 3D models.

Registration may include automatically analyzing the surface(s) (or in some cases internal structures, e.g., using near-IR data) of the 3D model to identify multiple consistent regions that may be used for registration of the 3D models. This may be performed algorithmically (e.g., using a convolution of 3D models to identify relatively invariant landmarks) and/or using a machine learning agent trained to identify invariant landmarks between the different 3D models. Once the landmarks are identified, the correspondence relationship may be determined by registering the landmarks between the different 3D models ("registration"). The 3D models may then be aligned or matched. In some cases the 3D models may be set to a common coordinates system. Shape correspondence may be performed in any appropriate manner, including (but not limited to) patch deformation learning, point translation learning, the use of a shape deformation network, the Laplace-Beltrami eigenfunctions of a functional maps framework, unsupervised point cloud shape correspondence, and/or the use of a self-assembling orientation-aware network. In some cases the matching or correspondence may be determined by setting or hypothesizing an initial correspondence between the two 3D models (e.g., in some examples between the mesh clouds), using the initial correspondence to determine a transformation between the two, apply the transformation to one of the two 3D models to produce a transformed model, and compare the transformed 3D model to the other (untransformed model), if the comparison is not within an acceptable range, modifying the correspondence and repeating this process (e.g. iterate) until the comparison is within the acceptable range. Since the 3D models are taken at different times, and may be taken by the same or by different scanners (e.g., intraoral scanners), the mapping may not be precise.

In any of these methods, the ROI identified in the first 3D model may be mapped onto the other (one or more) 3D models 107. In some cases, if a correspondence relationship has been determined, the correspondence relationship may be used to map the ROI onto the one or more additional 3D models (e.g., onto the different intraoral scan data sets). Alternatively, in some examples, the ROIs may be mapped to the additional 3D models without requiring an explicit determination of the correspondence between the various 3D models for each different time. For example, the ROI may be mapped to different 3D models by identifying one or more relatively invariant landmarks near the ROI (e.g., teeth or regions of teeth) and identifying the corresponding ROI region. In any case, the method may include mapping the ROI onto the different 3D models.

Once the ROI has been mapped to the one or more 3D models corresponding to additional intraoral scans taken at different times, representative images may be generated for each of these one or more 3D models 109, using the same technique described herein for generating the first representative image. For example, the representative 2D image for each additional set of intraoral scan data may be taken (e.g., selected) from the 2D scans of the set of intraoral scanning data or it may be synthesized from the 2D scans of the set of intraoral scanning data. The method may include finding points corresponding to one or more of the plurality of points defining the ROI (or an outline of the ROI) in each of a plurality of 2D scan images of the set of intraoral scan data (e.g., the scans corresponding to the at least the portion of the 3D model including the ROI), and generating a representative 2D image, wherein the representative 2D image includes the maximum number of the points defining the ROI (or the outline of the ROI) and/or has a corresponding camera angle that is approximately normal to a surface containing the ROI in the 3D model.

Once the additional representative images have been generated, they may be modified 111. For example, the representative images may be modified to better match each other, e.g., to make it easier to perform a direct comparison between the images. For example, the methods may include adjusting or normalizing the intensity of the representative image, cropping or resizing the representative images, etc. In some cases the method may include converting the images into more photorealistic images. In some cases the field of view of the representative images may be made larger or smaller. The methods described herein may include combining the representative images into a time-laps set of images that may be viewed as a loop or video. Optionally, as mentioned, in some cases additional intermediate representative images may be synthesized and included in the combined set of representative images.

The representative images may be stored (e.g., in a local or remote memory), transmitted (e.g., to a remote server, to a user's medical/dental record, etc.) and/or may be displayed 113. In any of these methods and apparatuses, measurements may be taken from either the representative images, from the 3D model and/or from the scan images of the set(s) of intraoral scans associated with the representative images and 3D models. For example, these methods may determine a change in the shape or size (e.g., volume) of a dental condition (e.g., caries, crack, etc.) within the ROI and/or of the ROI itself.

Region of Interest

In general, the methods described herein may allow the selection of the region of interest (ROI) as a point or region from the 3D scan using a user interface. The region of interest may be of any size, and in particular, may be relatively small. The boundaries of the ROI may be regular (e.g., a circular, oval, rectangular, or other shape, which may be projected onto the 3D model surface) or irregular. As mentioned, the ROI may be set by or adjusted by the user. For example, the user may manipulate, via a user interface (UI) a display of the 3D model of the teeth taken at the first time period (first intraoral scan) and may either select a region (direct selection) by may place a marker onto a region; in some examples the size and/or shape of the ROI around the marker may be automatically generated. In some examples, the user may indirectly select the region by zooming in on a region or dwelling on a region. Another indirect selection may include automatically selecting a region from an approximate center of the displayed 3D scan (e.g., 3D model representing the 3D scan).

Figure 2B:
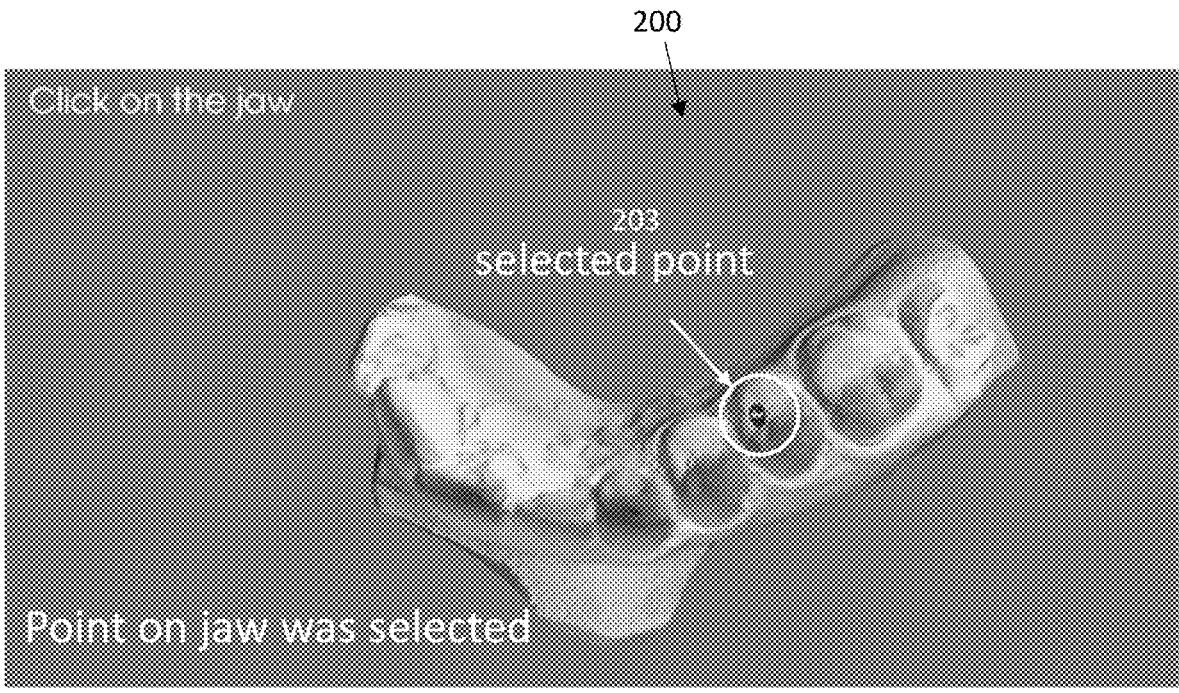

FIGS. 2A-2B illustrate one example of a method of selecting a region of interest for performing a longitudinal analysis. In FIG. 2A the user interface 200 illustrates display of a 3D model of at least a portion of a patient's jaw from an intraoral scan. The user may manipulate (e.g., rotate, zoom, pan, etc.) the 3D model within the window of the user interface. As shown in FIG. 2B, the user may select a region of interest (ROI) by selecting a point 203 on the surface of the 3D model. As described above, this point may be used as the center of the region of interest as described herein.

Representative Image

Once the region of interest is selected from the first 3D model of the patient's teeth, a "best" representative two-dimensional (2D) image may be selected or generated that shows the selected region of interest. The best representative 2D image may be selected from intraoral scanner images used to form the first 3D model (e.g., taken by the intraoral scanner), or it may be generated as a synthetic image from these scan images and/or the 3D model. For example, the first representative 2D image may be selected from the actual images taken by the intraoral scanner and may be selected by either automatically or semi-automatically as best illustrating the region of interest. For example, the representative 2D image may be selected by identifying an image that includes the most points forming the ROI, or in some examples the boundary of the ROI. Alternatively or additionally, in some examples the representative 2D image may be selected by having the camera angle relative to a surface containing the ROI in the 3D model that is most normal to this surface. For example, the first representative 2D image may have a camera angle relative to a surface containing the ROI in the first 3D model that is approximately normal to the surface containing the ROI in the first 3D model.

For example, a representative image may be selected from intraoral scanner images used to form the 3D model (e.g., the first 3D model) by identifying which of the intraoral scanner images best map to the ROI identified from the first 3D model (the target ROI). In practice this may be done by optimizing to identify which of the intraoral scanner images include features arranged most like the features from the target ROI. For example, feature within (and/or near) the region of interest may be identified, and their distances and angles may be measured or estimated. These distances may be used to determine as an arrangement of features that may be identified based on their relative proximity and angle in the putative scans. For example, the features and their relative distances and may be identified from the intraoral scan images and their relative arrangement (distances and/or angles) may compared and putative representative images may be ranked by identifying those with minimum differences. In some cases the direction of change between the target ROI and the putative representative images may be used to select the representative image, for example, by identifying images in which the relative changes between features are similar. The transition between the putative representative image and the target ROI may be optimized, so that, when transitioning between the target ROI and the putative representative images (e.g., in an animation) the transition is smooth and relatively continuous (e.g., not jumpy). In performing this process, the target features may be weighted, and the error between the target ROI and the putative images may be scored based on this weighting. Target features may be features on the teeth (e.g., local morphological features such as pits and fissures, peaks, cracks, bumps, color/discoloration, etc.). The weights on the targets may be used to determine a weighted average minimal error. Other minimizations can be using limits of maximal error per target.

Alternatively, in some variations, the representative 2D image may be synthesized from the 3D model, and/or the plurality of corresponding 2D images taken by the intraoral scanner for that time period. For example, the representative 2D image may be generated using a plurality of the 2D images that include many (or all) of the points forming the ROI, or in some examples, the boundary of the ROI, and a camera angle relative to the surface containing the ROI in the 3D model that best shows the ROI. In some examples this camera angle may be approximately normal to the surface containing the ROI in the 3D model. One or more techniques for generating the synthetic image may be used, including, but not limited to the use of a trained neural network to generate the synthetic first representative image, such as local light field fusion ("LLFF"), neural radiance fields ("NERF"), scene representation networks (SRN), etc.

The putative representative image may be verified and/or adjusted. In some examples the putative representative image may be adjusted to adjust the field of view, e.g., to adjust the field of view to show more, or less of the adjacent surrounding region(s). The putative representative image may be adjusted automatically or by the user. For example, optionally any of these methods may automatically determine a putative representative image as mentioned above, and my present the putative representative image to the user (e.g., dental professional, technician, patient, etc.) and allow the user to accept, reject or modify the representative image. In some examples a user interface may present the putative representative image and allow the user to adjust the putative representative image. In some examples the user may adjust the angle (e.g., camera angle) of the putative representative image showing the ROI. The new putative representative image may be calculated or determined using the new camera angle. In some examples this process may be repeated continuously, including displaying and allowing the user to change the camera angle for the putative representative image. Alternatively or additionally the user interface may allow the user to reselect of modify the ROI and the process of determining the putative representative image may be repeated.

Once the first representative image is determined, the second (or more) representative images taken from different times may be determined. This may be done using the camera angle of the first representative image and the 3D model. This technique may be particularly advantageous, because it allows for very quick processing as compared, and results in significantly closer matching between the images taken at different times, improving the longitudinal analysis.

For example, a second representative image may be determined by first identifying points on the second 3D model corresponding to points defining the ROI (e.g., the points forming the ROI, or in some examples, the boundary of the ROI), and determining a representative two-dimensional (2D) image that shows these points, as described above. The points on the second 3D model may be determined by using the correspondence relationship ("correspondence") between the first 3D model and the second 3D model, as mentioned above. For example, the ROI (or the points determining the ROI) in the second 3D model may be identified from the region corresponding to the ROI in the first 3D model by transforming the first 3D model so the ROI may be mapped to the second 3D model.

In some examples a correspondence between the first 3D model and the second 3D model may be determined. Correspondence between multiple 3D models may identify meaningful relations (or mappings) between elements of the 3D models, including the teeth. This may be referred to as registration, alignment, or matching. Shape correspondence may be performed in any appropriate manner, including (but not limited to) patch deformation learning, point translation learning, the use of a shape deformation network, the Laplace-Beltrami eigenfunctions of a functional maps' framework, unsupervised point cloud shape correspondence, and/or the use of a self-assembling orientation-aware network. In some cases the matching or correspondence may be determined by setting or hypothesizing an initial correspondence between the two 3D models (e.g., in some examples between the mesh clouds), using the initial correspondence to determine a transformation between the two, apply the transformation to one of the two 3D models to produce a transformed model, and compare the transformed 3D model to the other (untransformed model), if the comparison is not within an acceptable range, modifying the correspondence and repeating this process (e.g. iterate) until the comparison is within the acceptable range. Since the 3D models are taken at different times, and may be taken by the same or by different scanners (e.g., intraoral scanners), the mapping may not be precise.

Once the points on the second 3D model corresponding to the points defining the ROI (e.g., the points forming the ROI, or in some examples, the boundary of the ROI) the second representative image may be determined, as described above. In some examples the second representative image may be selected from intraoral scanner images used to form the second 3D model (e.g., taken by the intraoral scanner used to generate the second 3D model. For example, the second representative 2D image may be selected from the actual images taken by the intraoral scanner and may be selected by either automatically or semi-automatically, as best illustrating the region of interest as transformed to the second 3D model. In some examples, the second representative 2D image may be selected by identifying an image that includes the most points forming the transformed ROI, or in some examples, the boundary of the transformed ROI. Alternatively or additionally, in some examples the second representative 2D image may be selected as having the same (or approximately the same) camera angle relative to a surface containing the transformed ROI in the second 3D model; for example, the second representative 2D image may have a camera angle relative to a surface that matches the camera angle of the first representative 2D image.

Preferably, the second (or more) representative 2D image (s) may be generated as a synthetic image using the second 3D model, and/or the plurality of corresponding 2D images taken by the intraoral scanner to generate the second 3D model. For example, the additional representative 2D image (s) may be generated using a plurality of the 2D images that include many (or all) of the points forming the ROI, or in some examples, the boundary of the ROI, and the same camera angle relative to the surface corresponding to the first representative 2D image. One or more techniques for generating the synthetic image may be used, including, but not limited to the use of a trained neural network to generate the synthetic first representative image, such as local light field fusion ("LLFF"), neural radiance fields ("NERF"), scene representation networks (SRN), etc.

Synthetic Images

In general, the methods and apparatuses described herein may generate synthetic images from the scans of the intraoral scan data. In some cases synthetic images may be generated to provide images from camera positions and/or camera angles that were not explicitly included in the set of intraoral scanning data. When collecting the intraoral scanning data the scanner may be moved over the patient's teeth in a pattern that provides overlapping images of the teeth from different positions taken along different pathways around the teeth. Thus, a synthetic image or images of the teeth may be generated from a position and/or camera angle that is different from the actual positions and camera angles taken while scanning.

In addition, in some cases the field of view of the actual scan images for the set of intraoral scan data may be different, including smaller than, other images or images taken by other intraoral scanners. Thus, also described herein are methods of generating synthetic having different fields of view. For example synthetic ('novel') images or views may be generated from intraoral scans using a plurality of (e.g., 3 or more, 4 or more, 5 or more, 6 or more, etc.) images of acquired during the scan. These different acquired images may be different color channels (e.g., red, blue, green, etc.). In general, synthetic images may be generated after post processing from the intraoral scanning. In some cases intraoral scanner apparatuses may include multiple cameras each collecting images; the different images may be taken from the different cameras that may be simultaneously or nearly simultaneously recording. In some cases the intraoral scanner may be positioned very close to the teeth when scanning, e.g., the pinhole of the camera may be located approximately 7 mm above the teeth compared; although intraoral scanners may include a very wide angle, these factors may, in some cases, result in perspective distortions. This may make it hard to understand from a single image alone where are we located in the jaw and to understand clinical findings in the image. Generating a novel view from given position in which the field of view is too narrow may be made difficult by concealment. An image to the left of the desired position may not include things which are to the right of objects due to concealment. This problem may be avoided by using cameras that are situated behind, in front, left and right to the desired novel view. In some cases, a camera situated behind and in front to the desired production position may be used. In some cases, a minimum of three cameras to cover all directions may be used. For example, these methods for generating a wider field-of-view synthetic image may use three images that look at the same scene, and their chief ray directions may form a triangle which contains the chief ray direction of the desired synthesized image. In addition to the surrounding triangle formation, the area field of view may be a distance of, e.g., approximately 10 mm from the pinhole camera intersection. After acquiring the input images, the images may be projected to a grid which is contained from number of planes parallel to the screen of novel view camera. Each point in the screen may correspond to a pixel on the novel view image. After the images are projected onto the grid, a tensor of size image width, image height, and number of planes. The resulting "image soup" may be supplied to a trained neural network using a "leave one out" cross validation method. For example, the method may include taking one image out form a grid by projecting 3 neighboring images and trying to predict the image which we took out. The neural network may be used to generate a larger field-of-view image.

In some example, all or some of the representative images may be synthetic images. In addition, any of these images may be photorealistic images. For example, the field of view of the representative images may be made larger or smaller, as just described. For example, the field of view may be panoramic, or maybe a sub-region of a panoramic view.

Processing of Representative Images

Figure 3A:
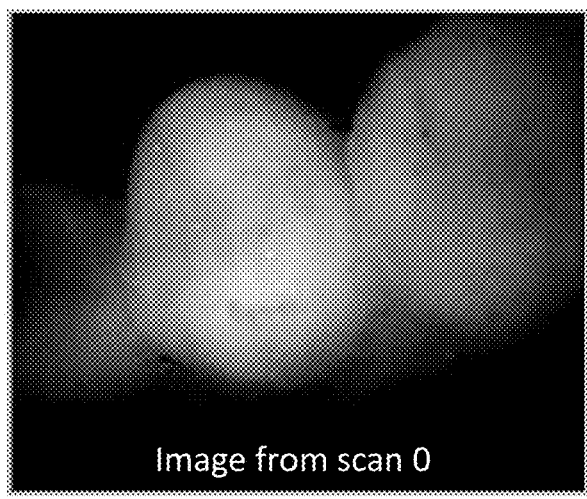
FIGS. 3A-3C illustrate examples of representative images from two different sets of intraoral scan data.
Figure 3B:
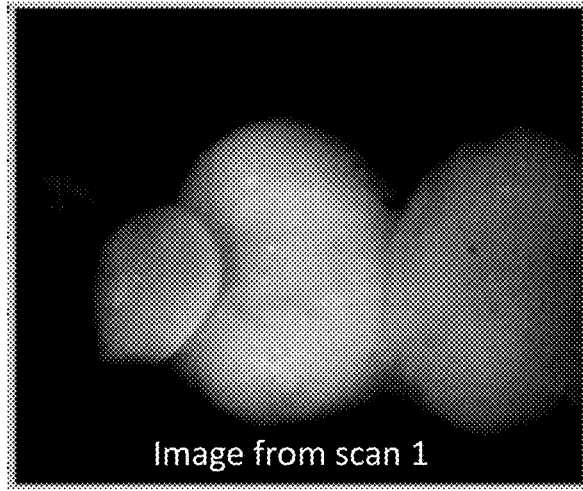
Figure 3C:
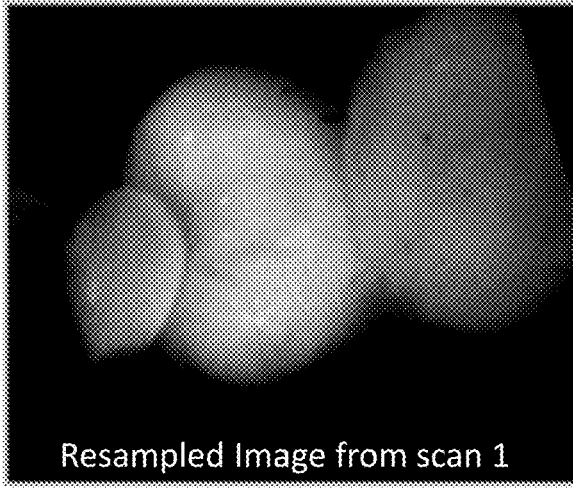

Once the representative images have been determined, in some examples the images, which show the ROI at different times, may be further corrected for display, storing, transmission and/or further analysis. For example, any of the first representative image and the second representative image may be adjusted to correct the perspective (perspective correction) a rotation relative to the teeth, and/or the colors may be adjusted (e.g., color equalization, saturation, brightness, hue, etc.). The representative images may be adjusted so as to be as similar to each other as possible. In some examples both the first representative image and the second representative image are adjusted. FIGS. 3A-3C illustrate one example of a method for adjusting the representative images. FIG. 3A shows the representative image from the first set of intraoral scan data ("scan 0"). In this example, the scan is an intraoral scan using near-IR light. A second representative image may be determined as described herein for the second set of intraoral scan data ("scan 1"). As shown in FIG. 3B the representative image is slightly rotate, and is at a slightly smaller scale relative to the first representative image shown in FIG. 3A. Thus, the second representative image may be adjusted, e.g., by resampling, to better compare with the first representative image, resulting in the image shown in FIG. 3C. Once the representative images have been post-processed to allow direct comparison, they may be further processed to present them as part of a display for comparison, as shown in FIGS. 4A-4G.

In general, the sets of intraoral scan data (which may include 3D models and 2D scans) may be any appropriate scan, including surface (in some cases, visible-light, e.g., white-light) scans, near-infrared (NIRI) scan, florescent scans, x-ray scans, etc., including combinations of these. Although many of the examples described herein are specific to intraoral scanners (and may be particularly well suited for intraoral scanners) these methods and apparatuses may be adapted for use with other scanners. The set of intraoral scan data may include surface scan, or in some cases a volumetric scan, which includes both surface and internal (e.g., volume) data. In some example the set of intraoral scan data may include a 3D model, such as a point cloud model or other representation based on the set of intraoral scan data.

In many of the methods and apparatuses for performing these methods described herein, the region of interest (ROI) may be determined and tracked on the 3D model of the set of intraoral scan data (e.g., surface scan, volumetric scan, etc.), for example, using of the 3D model of the jaw to identify corresponding regions of different 3D models taken at different times. The comparison between the different scans may be presented by comparing the representative 2D images. Any number of different times may be compared. These times may be taken at regular intervals (e.g., every x days, weeks or years, where x may be 1, 2, 3, 4, 5, 6, 7, 9, 10, etc.). These times may be taken at irregular intervals. The times may correspond to treatment stages of an orthodontic treatment plan (which may include times before/after the treatment plan).

In general the comparison may be a display to a user (dentist, orthodontist, dental professional, technician, etc.). In some cases the user may be the patient. The comparison may be transmitted and/or stored. When displayed, the comparison may be made using a user interface that is configured to display the representative 2D images side-by-side, as a video (e.g., sequential, overlaid display), or the like. In some examples, the output may comprise a looping video showing the time sequence of the representative images. The time sequence may be ordered (e.g., earliest to latest, latest to earliest). For example, FIGS. 4A-4G illustrate an example of a set of representative images (scan 0 to scan 1) from two sets of intraoral scan data taken at two different times. In the example display shown, the second representative image (from the scan 1 set of intraoral data) may be shown over an image of the first representative image (from the scan 0 set of intraoral data), and the transparency of the second representative image (scan 1) may be adjusted by the user operating a control (e.g., a slider 404, dial, etc.) to show the transition 406 between the first representative image and the second representative image.

The methods and apparatuses described herein may be used with an intraoral scanner. In some examples, these methods and apparatuses may be integrated into an intraoral scanner.

These methods and apparatuses may be used as part of a treatment. For example, these methods and apparatuses may be used as part of a method or apparatus for the detection or tracking of one or more dental conditions, such as, but not limited to caries, cracks, plaque, etc., and the features may be tracked over time. The method may be used with or may include using a features detection map such as a caries detection severity map. A caries detection severity map may be used to compare severities of caries over time. For example, the region of interest may include the one or more carries. In some examples the region of interest may be automatically or semi-automatically detected based on the presence and/or severity of one or more caries present on a caries detection map. Any of these methods may include generating a features map (such as a caries detection map) and setting the region of interest based on the one or more regions identified as having carries. The one or more regions may be determined based on the severity of the detected one or more carries. The feature may be initial detected in the earliest time scan (set of intraoral scan data). In addition to visually tracking the feature(s), such as carries, over time, these method and apparatuses may also determine one or more quantitative and/or qualitative measurements from the representative image(s) from different times. For example, an area measurement for the feature(s) may be taken for comparing at different times (e.g., the area of a lesion), or by determining a confidence score for the one or more lesion. The quantitative and/or qualitative data may be stored, transmitted and/or displayed. The quantitative data may be presented as a graph, chart, table or the like. In general, the method and apparatuses may mark the one or more features in the representative 2D images. For example a lesion (e.g., one or more carries, cracks, etc.) may be colored, outlined, highlighted, labeled, etc. for each of the different representative 2D images.

In general, the methods and apparatuses described herein may include displaying the representative 2D images for different times using any appropriate method or technique. The images may be shown side-by-side (adjacent to each other) and/or atop each other, in which one or more images are made partially transparent. Alternatively or additionally, the representative images may be shown as a sequence or loop (e.g., a video loop) in order of their respective times (e.g., the time periods that the related set of intraoral scan data were taken). The representative images may be compared to each other by image processing, such as image subtraction, image correlation, etc. In some cases the methods or apparatuses described herein may compare the representative images or regions of the representative images (e.g., the ROIs within each image) and output data regarding the differences between the representative images representing different times. The output data may be included as part of the display, or it may be separate from the displayed representative images. In some examples the output data may be displayed on (as text, images, highlights, etc.) the one or more representative images.

Figure 5:
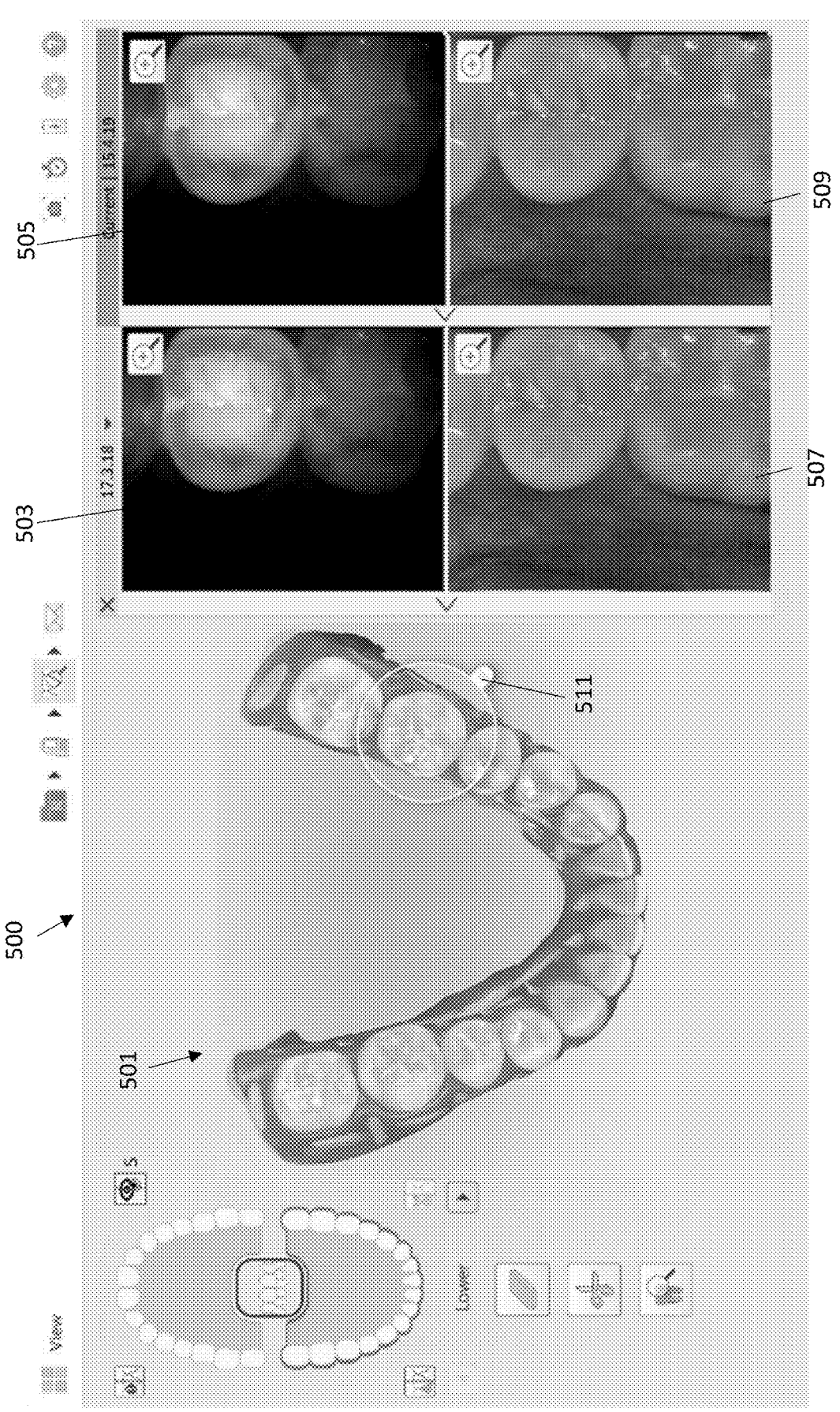
FIG. 5 illustrates one example of a user interface including a display showing representative images.

For example, FIG. 5 shows one example of a user interface 500 showing a 3D mode of a patient's dental arch 501 (e.g., a first 3D model, derived from a first intraoral scan) on the left side of the user interface. The 3D model also illustrates regions that have been highlighted, e.g., to show dental conditions. A region of interest 511 (shown as a loop) encompassing the region between two molars, is also shown. Using the techniques described herein representative images including this ROI have been determined for both an initial scan (taken at a first time and resulting in a first set of intraoral scan data) and a second scan (taken at a second time and resulting in a second set of intraoral scan data). In this example, representative 2D images are shown for both near-infrared light images 503, 505 and for white light images 507, 509; the first representative images (both near-IR 503 and white light 507) are shown on the left, with the second representative images (near-IR 505 and white light 509) are shown on the right. The two scans (and resulting sets of intraoral scan data) were taken just over a year apart.

The graphical user interface (GUI) shown in FIG. 5 may be modified as described herein to display the identified regions of interest. For example, any of these methods and apparatuses may include showing one mode of illumination; in FIG. 5 the left panel shows a color image of the teeth (as a 2D projection of the 3D model) with region, so interest highlighted. The right four images show near-infrared images (top) and color (e.g., RGB) images (bottom). In some examples only one modality (e.g. near-IR, while light (WL) or ultraviolet (UV)) may be individually shown. In some examples a single pan for two or more images, taken from the same modality (e.g., near-infrared, white light, ultraviolet, etc.) may be alternately shown, flickering between them at a rate of 1 Hz, 2 Hz, 3 Hz, 4 Hz, 5 Hz, 10 Hz, etc.).

As mentioned above, in general, the representative images described herein may be synthesized from the set of intraoral scan data (including from the collection of 2D images corresponding to the 3D model of the set of intraoral scan data), for example by rendering texture mapping from multiple 2D images and taking into account the camera position at the time of image capturing, and using a trained neural network to generate the images taken from a desired camera position. The desired camera position may generally be optimized based on the identified (automatically, manually or semi-automatically) region of interest. In addition, any of these methods and apparatuses may also generate synthetic intermediate representative images between the specified time regions; these synthetic intermediate representative images may be generated for time periods between the specified time periods of the sets of intraoral scan data. For example, if an intraoral scan (e.g., generating a set of intraoral scan data) is taken at time 0 (e.g., an initial intraoral scan), at a time of 6 months later (e.g., second intraoral scan), and at a time of 2 years later (e.g., third intraoral scan), one or more synthetic intermediate representative images may be generated for times between 0-6 months (e.g., at three months, every month, etc.) and/or for times between 6 months and 2 years (e.g., at one year and 1.5 years, every month, etc.). These synthetic intermediate representative images may be displayed as described herein. The synthetic intermediate representative images may be generated by extrapolating between the actual synthetic intermediate representative images. In some examples a second trained neural network may be used to generate the synthetic intermediate representative images; this second trained neural network may be trained on time sequences of 2D images showing changes in dental regions over time.

The methods and apparatuses described herein may compare one or more features from a clinical finding, such as caries, cracks, misalignment of teeth, etc. over time. In some examples clinical findings may be automatically or semi-automatically detected. For example one or more clinical features may be input or identified by a user. In some examples, the one or more clinical features may be determined or identified from the patient's teeth using a trained neural network (configured as an autoencoder, or a trained autoencoder) to identify these one or more clinical features. The clinical features may generally be invariant to camera position. In some examples the trained neural network may be used to identify one or more clinical features, and these one or more clinical features may be used to automatically or semi-automatically (e.g., by asking the user to confirm after displaying) determine or set the region of interest from one or more of the 3D models. One of the 3D models (and/or the 2D images corresponding to the 3D model) may be reviewed by the trained neural network to identify or flag possible clinical features; the identified possible clinical features may then be used to set one or more regions of interest, and the procedures described above may be used to generate the representative images corresponding to scans taken at different times of the same ROIs. Thus, by encoding features of a clinical finding (for example by training autoencoder) which are invariant to camera position these methods and apparatuses may compare the encoded features at different times. The trained neural network that may be used to identify clinical features (e.g., features related to a clinical finding) may be different from the trained neural networks described herein that may generate synthetic intermediate images. For example a trained neural network that may be used to identify one or more clinical features may be referred to herein as a clinical features trained neural network. The clinical features trained neural network may be augmented (e.g., trained) with images including identified clinical features and, in some examples, the same clinical finding from different times.

Any of these methods and apparatuses may be configured to use volumetric models (e.g., volumetric models of the teeth and/or other regions of the intraoral cavities). Volumetric models may be derived from penetrative scans, such as X-rays (e.g., cone beam tomography, standard x-rays, etc.), infrared light (e.g., near-IR light), etc. Thus, in some cases the 3D models may include internal (volumetric) data, in addition to surface data. In some cases the volumetric model (3D volumetric model and 2D scans corresponding to these) may be used to compare lesions volumes directly. For example, the volumes of lesions over time may be determined using volumetric 3D models and/or the representative images identified as described herein.

Although the examples of methods and apparatuses described herein typically described the use of intraoral scans taken at different times from the same (or more likely, the same type of) intraoral scanner, any of these apparatuses may be used instead to compare across different scanner, including different types of scanning modes (e.g., Near-IR, color, x-ray, florescent, etc.). In some cases these methods and apparatuses may compare severity maps having the same field of view. For example, one method of doing so may compare images to have the same field of view and then to compare severity maps. Using severity maps (or any kind of invariant features) may allow comparison of severities from different capturing devices. For example, the methods and apparatuses described herein may compare between different intraoral scanners, including different intraoral scanning mode.

Apparatuses

As described above, an apparatus may be configured to perform any of the methods described herein. In general, these apparatuses may include one or more processors and hardware, software and/or firmware for performing any of these methods. In some examples the apparatus may be configured as an intraoral scanner that may be configured to longitudinal display and/or analysis of intraoral scan data.

Figure 6:
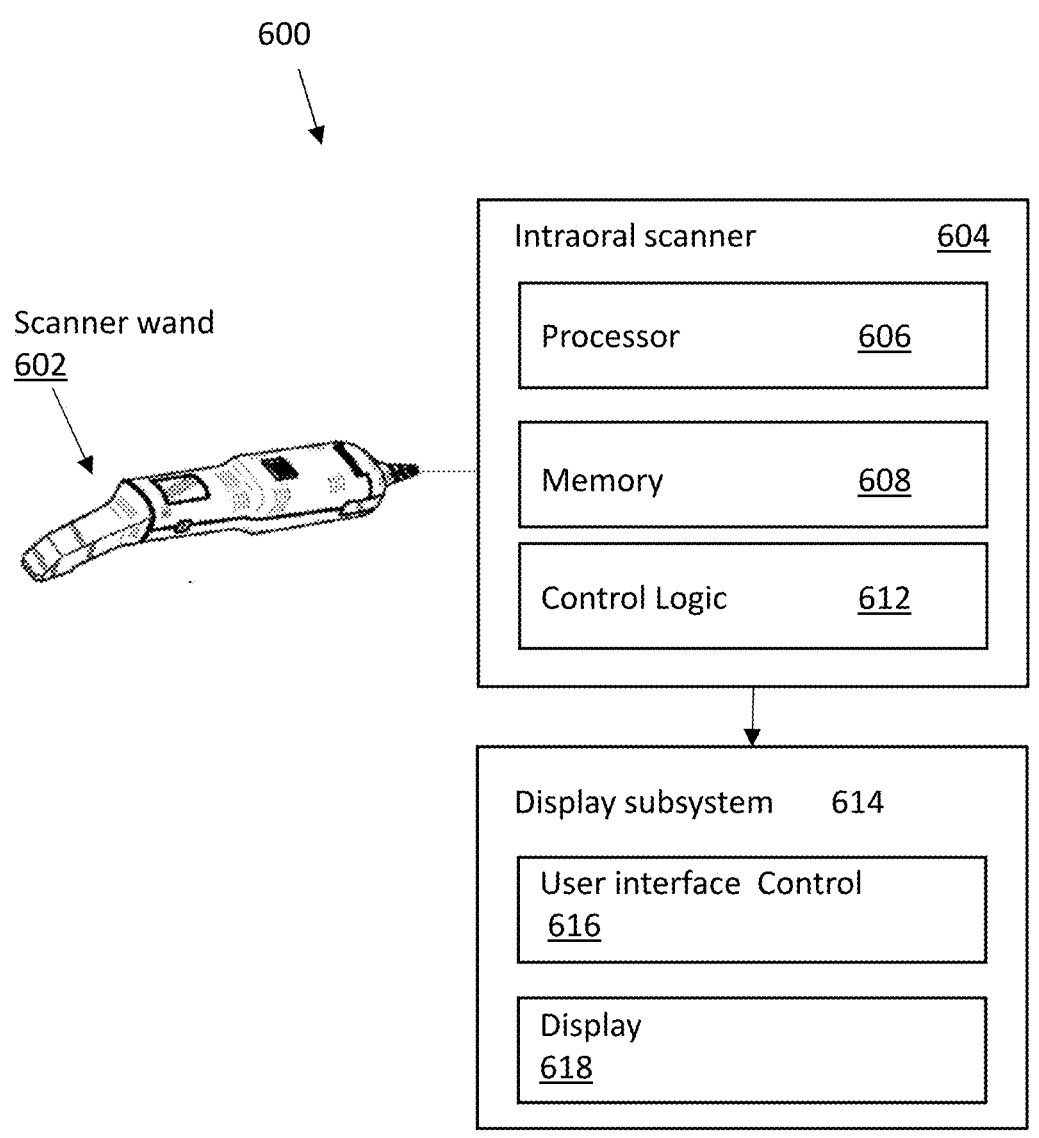
FIG. 6 illustrates one example of an apparatus for generating a longitudinal series of intraoral images as described herein.

For example, FIG. 6 schematically illustrates one example of an apparatus that is configured to generate longitudinal comparisons of intraoral scan data. In FIG. 6 the apparatus may include or may be configured to connect to an intraoral scanner 604, including a scanning wand 602 or other element including the scan head for scanning the patient's teeth. The apparatus may generally include or be coupled to one or more processors 606 that may execute the software, e.g., a non-transitory computer-readable medium comprising instructions which, when executed by one or more processors, causes the one or more processors to perform a method as described. The one or more processors may include microprocessors. The software may be included on a local or remote memory 608 and my include instructions for all of some of the steps described herein. The memory may store and/or access control logic 612 including all or some of the steps (see, e.g., FIGS. 1A and 1B) in these techniques. The steps may access one or more engines (e.g., a correspondence engine, an ROI identification engine, a 3D to 2D mapping module, a representative image generation module, a synthetic image generation module, a comparison module, etc.).

In the example shown in FIG. 6, the non-transitory computer-readable medium comprising instructions which, when executed by one or more processors, causes the one or more processors to perform a method comprising. According to the example shown in FIG. 6, the apparatus may (optionally) be integrated into an intraoral scanner 604 including a scanning wand 602. In use, the instructions and/or any executing modules, may be performed by the apparatus 600, including identifying a plurality of points defining a region of interest (ROI) on a first three-dimensional (3D) model of a patient's teeth taken over a first time from a first set of intraoral scan data, wherein the 3D model is derived from a first set of intraoral scanning data taken using an intraoral scanner. The apparatus may also be configured to find correspondence between the first 3D model and a second 3D model of the patient's teeth form a second set of intraoral scan data taken over a second time. Finally, the apparatus may be configured to generate representative images from the first scan and one or more subsequent scans. For example, the software may be configured to find points corresponding to one or more of the plurality of points defining the ROI in each of a plurality of images corresponding to the first 3D model, and generating a first representative image that is two-dimensional (2D), wherein the first representative image includes a maximum of the plurality of points defining the ROI and/or has a corresponding camera angle that is approximately normal to a surface containing the ROI in the first 3D model, and generating a second representative image corresponding to the second 3D model, wherein the second representative image has to the same camera angle as the first representative image relative to the second 3D model as the first representative image and includes a region of the second 3D model that corresponds to the ROI.

The apparatuses described herein may also be configured to display the representative images and/or measurements made as part of the 2D images. In FIG. 6, the apparatus may include a display sub-system 614 that may receive, transmit and/or output the representative 2D images. The apparatus shown in FIG. 6 may include or be configured to couple to a user interface control portion 616 such as they have display, screen, etc. 618. For example, the apparatus may include modifying the first and/or second representative images to adjust one or more of: perspective, rotation or color equalization so that the first and second representative images match more closely to each other.

Longitudinal Analysis of 2D Images

The methods and apparatuses described herein may be used to track one or more regions of a subject's dentition. In general, a longitudinal comparison between two or more 2D images may use a 3D digital model taken from an intraoral scan as discussed above. Any two or more 2D images may be compared to allow detection and/or display of changes between the 2D images, even where the images are taken by different cameras, are synthesized (e.g., from a 3D digital model), and/or are taken at different times, when the dentition may have changed. In some cases this comparison may include determining and/or normalizing the camera positions for each of the 2D images. The camera position for any 2D image may be derived from a 3D digital model (mesh) of the subject's dentition that may be generated by an intraoral scan, as described above. Once the camera position (e.g., relative to the 3D model) is known, the images may be compared. Thus, the 2D images and/or 3D model(s) may be aligned. A variety of alignment techniques are described herein and may be used.

In some cases an optical flow technique, e.g., a dense optical flow technique, may be used to align two or more 2D images and/or 3D models. The optical flow may be the vector field between time-displaced 2D frames from a sequence. This vector field can be used for registration by image warping.

Because the images are taken at different times during a treatment (e.g., orthodontic and/or dental treatment), the dentition, and in particular the subject's teeth, may be different, making direct alignment difficult. For example, the teeth may have moved and/or may have changed shape (due to grinding/bruxism, fillings, chipping, etc.). In some cases the 2D images to be longitudinally compared may be aligned or registered, which may generally include determining the relative camera positions between the two or more images. Registration/alignment and/or determining the camera position may use surface features. For example, the 2D image(s) may be registered to the 3D model to allow comparison between the 2D image, even where the 3D model is taken at a different time (during a treatment) and may have different tooth positions/shapes. Thus, the 3D model may provide a basis for registering 2D images taken at different times from each other and/or from the intraoral scan used to generate the 3D digital model.

In any of these methods a displacement map (using the image pixels) may be generated. For example, the matching pixels between the 2D images (and/or a 2D projection of the 3D digital model) may allow comparison of the same regions of interest between the 2D images and/or 3D digital model. As mentioned, in any of these methods an apparatuses, the 2D image(s) may be registered to the 3D surface, and this registration may be used to determine the camera position corresponding to the 2D image(s), which may then be used to register the 2D images to each other. Finally, the 2D images may be modified (scaled, translated, projected, etc.) and compared to each other. This comparison may include aligning the two atop and/or adjacent to each other (e.g., side-by-side, etc.), forming a time-lapse loop, etc. As mentioned, the time-lapse loop may include synthesizing intermediate images between the two or more 2D images, showing a transition between the two; in some cases the transition may be smoothed.

In one particular example, a patient (e.g., subject) may have a preexisting intraoral scan and a resulting 3D digital model of the patient's dentition. For example, the intraoral scan may be taken prior to the start of a treatment. The patient may themselves take one or more images of their dentition during the course of a treatment, and these images may be compared to each other or to other (e.g., earlier) images of the patient's teeth. The intraoral scan may therefore be used to register and permit comparison of any number of 2D images taken at different times and/or stages of treatment.

For example, in some cases a patient undergoing an orthodontic treatment may use their personal camera (e.g., their phone) with or without a retractor (e.g., to retract the lips from the teeth) to take pictures of their dentition. In some cases a retractor may be used in combination with a smartphone (see e.g., US 2024-0008731-A1 and US 2022-0338723-A1, herein incorporated by reference in their entirety). The 2D images taken may be to track progress of a treatment. In some cases the methods and apparatuses described herein may be used to provide sufficiently accurate alignment that measurable data on dentition (e.g., tooth position, inclination, orientation, gum recession, cavity development, cracking, etc.) may be extracted from the 2D images by longitudinal comparison. These methods may provide sufficient accuracy so as to allow a resolution of less than 1 mm (e.g., showing accurate change with sub-millimeter resolution), e.g., less micrometer resolution. The use of the 3D digital model generated by a reference intraoral scan may allow this high degree of resolution. The methods and apparatuses described herein may permit quantified measurement with sub-millimeter (e.g., micrometer, 0.9 mm or less, 0.8 mm or less, 0.7 mm or less, 0.6 mm or less, 0.5 mm or less, 0.4 mm or less, 0.3 mm or less, 0.2 mm or less, 150 microns or less, 100 microns or less, 50 microns or less, etc.) resolution. Features such as tooth movement, gum recession, gum inflammation, tooth decay, tooth cracking, shape change, tooth color change, etc. may be identified and quantified.

In any of these methods and apparatuses, the method may include camera registration, using the 3D digital model for each 2D image, as described above. Camera registration may include determining camera position (e.g., relative to the 3D model/representation of the teeth), e.g., determining a location of the camera when the image was taken.

The 2D image(s) may be pre-processed. Optionally, 2D images may first be filtered to remove (or modify) pixels that are not part of the dentition, e.g., if a retractor is used, to remove the retractor from the image(s). In some cases the image may be segmented. For example, the 2D image may be segmented to identify all pixels to which each tooth belongs.

Figure 8:
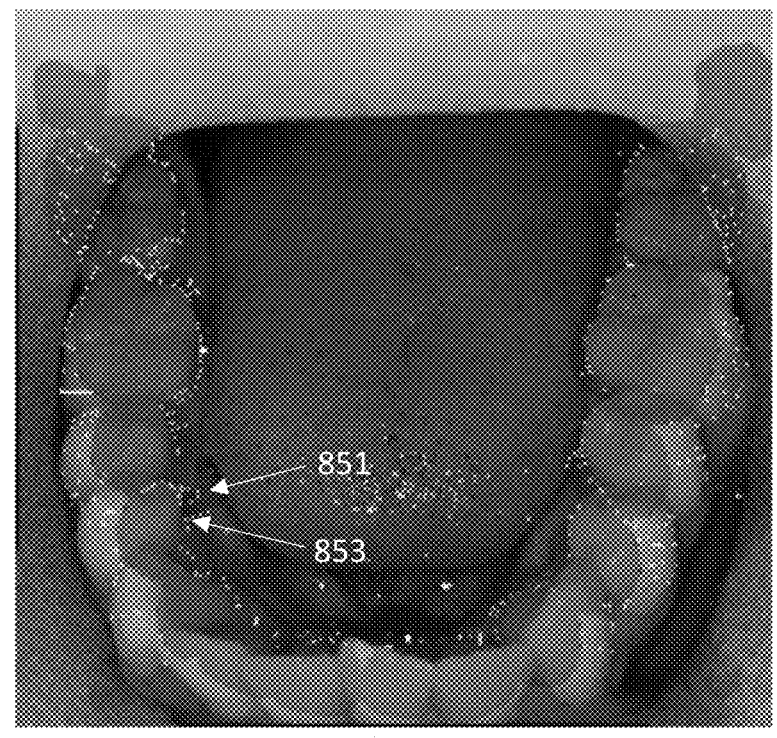
FIG. 8 show the 2D image of FIG. 7A in which silhouettes of the 2D image are compared with silhouettes of 2D projections from the 3D digital model (in FIG. 8 edge points are shown) to determine a fine alignment between the 2D image and the 3D digital model, e.g., to identify the camera position of the 2D image relative to the 3D digital model.
Figure 9:
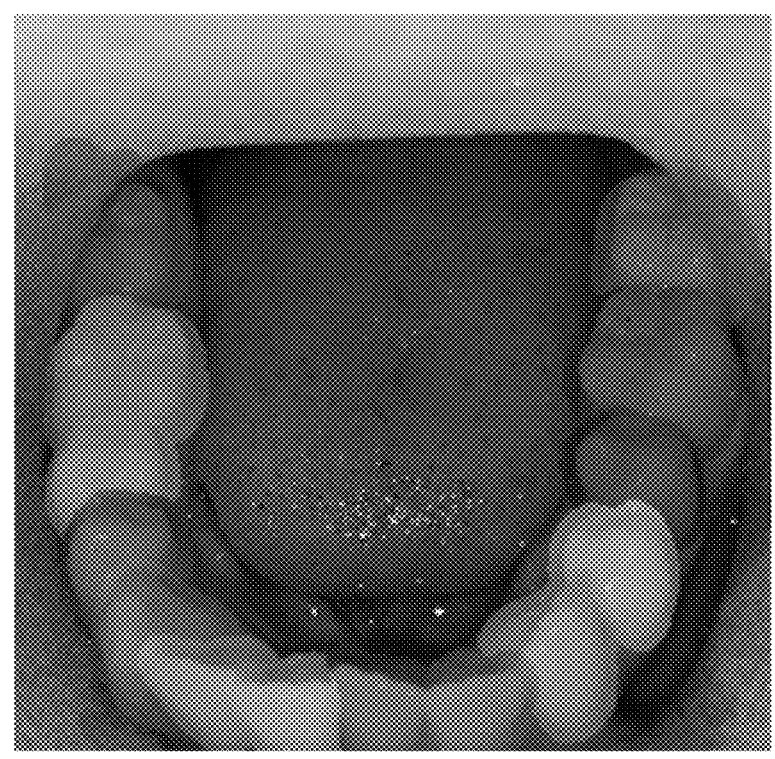
FIG. 9 shows the 2D image of FIG. 7A registered with the 3D model, showing the projected teeth semi-transparent over the 2D image.

In some examples the position and/or orientation of the camera relative to the 3D digital model of the dentition may be identified as described above. In some cases, the camera position corresponding to the 2D image may be determined by identifying characteristic features between the two, such as tooth center of mass. For example, the method may include identifying a coarse camera pose for the 2D image(s) by determining the centers of mass of the teeth in the image, as well as the centers of mass for individual teeth from the 3D mesh. In this example, the teeth in the 2D image may first be segmented to identify individual teeth. Further, the 3D digital model may be segmented to identify individual teeth. The centers of mass of each tooth may be estimated, and compared between the 2D image(s) and the 3D digital model. For example, FIG. 7A shows an example of a 2D image of a patient's dentition. The 2D image may be preprocessed as shown in FIG. 7B, to remove the non-tooth regions (pixels) and to segment the image so that individual teeth are identified (shown by different colors). The segmented image (e.g., FIG. 7B) may then be used to determine a center of mass for each tooth. FIG. 7C shows the original 2D image, on which the center of mass from the segmented 2D image are shown 780 along with the centers of mass of each tooth from the 3D digital model (mesh) 782, these centers of mass may be used to determine the camera position by optimizing so that the two dots corresponding to each tooth's center of mass overlap, e.g. so that the dots are as close as possible. This may provide a rough estimate of camera position. In some cases an optional additional refinement of the camera position may be made to provide fine alignment following this coarse alignment. FIG. 8 illustrates the use of silhouettes of the teeth for further alignment, to determine the location of the camera using the 3D digital model (mesh). In FIG. 8, the silhouettes from the 2D image are compared with silhouettes from projections of the 3D digital mode (having a camera positioned at known or synthetic camera images), are compared, to optimize matching as much as possible between the two, identifying a much more accurate estimate of the camera position. In FIG. 8, edge points for both the 2D images (e.g., camera image) and the edges from a projection of the 3D digital model are shown by colored dots indicating the edges of from the 2D image 851 and the projection of the 3D digital model 853, and the optimal overlap between the two may be used to determine the camera position accordingly (e.g., when the two edges, as defined by the edge points) are sufficiently close together. In FIG. 8, the 3D edge points are shown in a first color and the image edge point are shown in a second color). FIG. 9 shows the 2D image that has been registered with the 3D digital model, and individual teeth boundaries and teeth are shown by different colors.

Figure 10A:
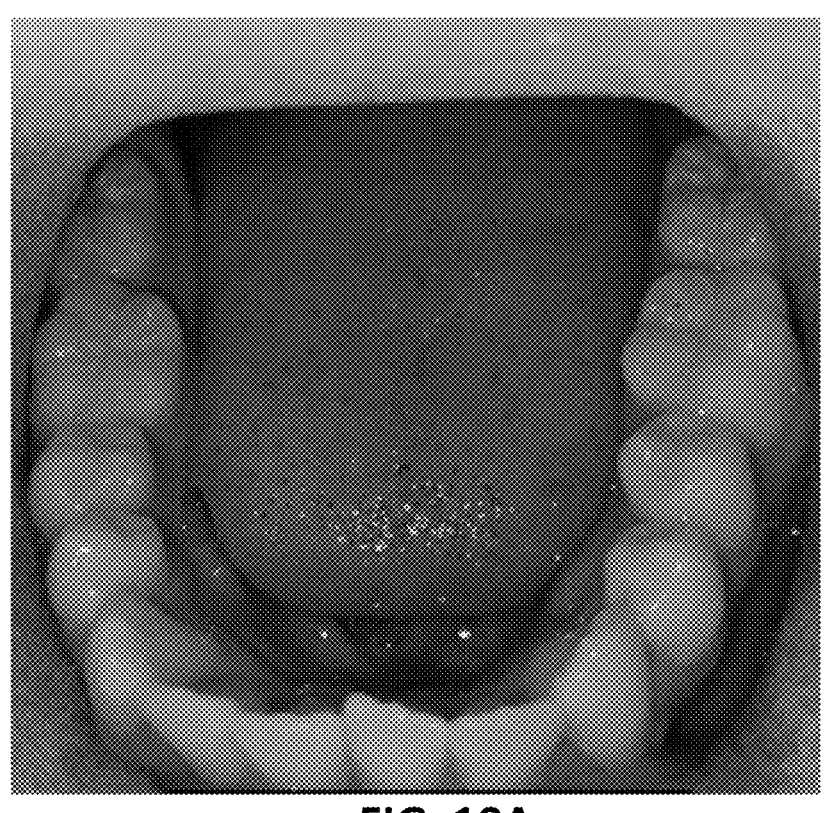
FIGS. 10A-10B illustrate another technique for registering the 2D image of FIG. 7A (shown again in FIG. 10A) with a 3D digital model (e.g. mesh model) taken by intraoral scan.
Figure 10B:
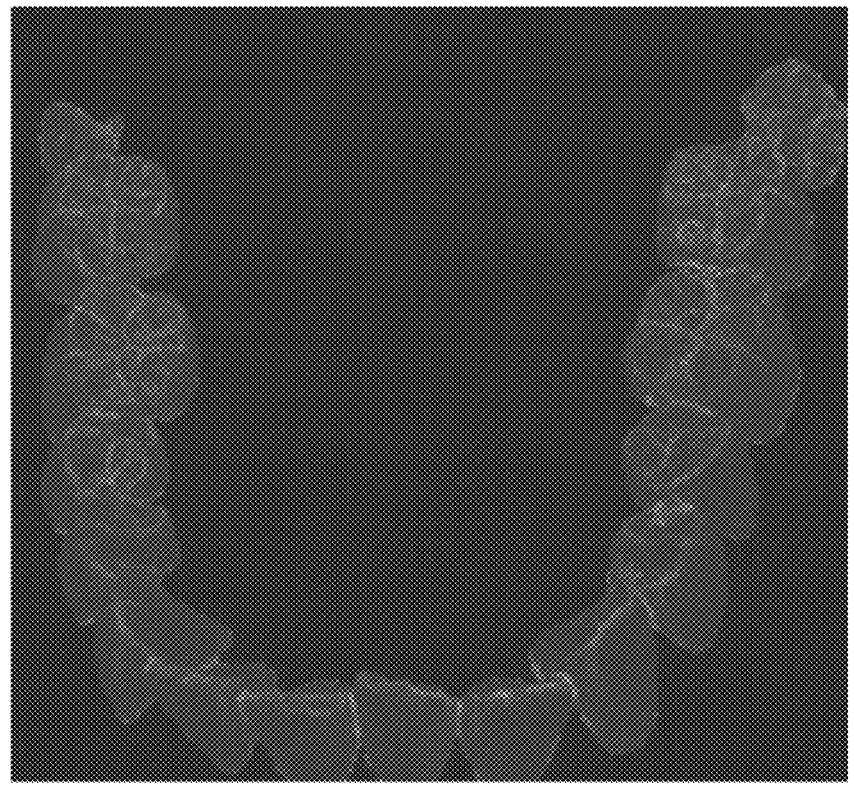

In some cases registration may be specific to a single tooth or group of teeth. For example, FIGS. 10A and 10B illustrate the use of other tooth features, such as cusps and fissures. In some cases it may be difficult to use just the silhouettes of the teeth or a single tooth, particularly where individual teeth (or just a few teeth) are used, and the silhouettes may not contain enough information. Thus, in some cases, to enrich the data from each image, the apparatus or method may identify the cusps and fissures in a 2D image (e.g., using a trained machine learning agent) that may compare these cusps and fissures to those from the 3D digital model. For example, in FIG. 10A a 2D image of the subject's teeth is shown. FIG. 10B shows an image in which the identified fissures and cusps from the teeth have been identified. The method or apparatus can then use the 3D scan of the jaw to register each image using the visible pattern of cusps and fissures to identify camera position (e.g., by matching cusps and fissures from the projected 2D images of the 3D model, for which cusps/fissures may also be identified, in some cases directly from the 3D model). This process may be expedited when the coarse alignment has been performed using a different feature (e.g., center of mass).

As mentioned, any of the steps described herein may be incorporated as a machine learning agent, such as a trained network, that may perform the identification and/or matching steps.

In some examples, these methods and apparatuses may include receiving and/or taking the 2D image(s) at one or more different times and may track changes in the dentition once the 2D image(s) are aligned using the 3D digital model as described above. The system may display this longitudinal comparison as described herein.

In some example these methods may be used to compare panoramic images (visible light, florescent, near-IR, etc.) over time. In any of these methods and apparatuses morphing may be used to show changes over time, as a first image may be morphed into the second image. Alternatively or additionally any of these methods or steps may include morphing two or more images into an intermediate position. Any of these methods and apparatuses may treat the upper and lower jaws separately, or may use them together, e.g., by adjusting the relationship between in the 3D digital model to match the separation between the upper and lower jaws.

Returning now to FIG. 1B, one method of generating a longitudinal comparison between one or more 2D images (e.g., images taken by a user) and/or a 3D digital model based on an intraoral scan is schematically illustrated. As described herein the longitudinal comparison may include a set of images including the 2D image(s) that either all share a common perspective, e.g., camera angle, or transition between two or more camera positions. The longitudinal comparison may include synthetic images that are generated from the 2D image(s) and/or the 3D digital model to allow smoot transitioning, e.g., morphing, over time between the 2D image(s) and in some cases a projection from the 3D digital model or a selected image from the 3D digital model.

For example, in FIG. 1B the method and/or an apparatus (e.g., system, device, software, etc.) may first take or receive one or more 2D images of a subject's dentition (e.g., teeth, gums, etc.) taken at different times, and optionally at different stages of a treatment plan 151. The method and apparatus may then identify the relative camera positions from which the one or more 2D images was/were taken. In some cases the 2D images are taken from a relatively similar position/orientation 153. These methods may use the 3D digital model as a reference to estimate an approximal camera position relative to the dentition in the 3D digital model as described above. Where there are multiple 2D images, a camera position relative to the 3D digital model may be determined for each of them. For example, a first alignment/registration may be performed for each 2D image with the 3D digital model by comparing one or more features (e.g., tooth center of mass, silhouette, facial axis of the clinical crown (FACC), etc.). between the teeth in the 2D image(s) and a series of projections of the 3D digital model 155. This process may be iterative, and may continue to generate projections of the 3D digital model until a best fit is identified, and may use the camera position for the projection as the identified camera position for that particular 2D image. The process may be repeated for each 2D image.

Optionally, a second (e.g., "fine") alignment/registration may be performed using a second feature, that is different from the first feature(s) for refining the identified camera positions 157. For example the second alignment/registration may be based on a comparison between the silhouettes, cusps and/or fissures, etc.

In instance where there are multiple 2D images, the camera positions at the different times corresponding to the 2D images may be compared. If the difference in position it too great for example, if the difference in position is so large that the features seen in each image have little overlap, then the method or apparatus may indicate that a longitudinal comparison is not reasonable. In some cases if the difference is small (e.g., less than a threshold that may be adjustable), a consensus camera position may be determined, and the 2D images may be modified (e.g., morphed) to allow smooth comparison between the two (or more) 2D images 159. Alternatively, in some cases the method or apparatus may generate one or more (e.g., a time series) of intermediate images morphing/transitioning between the different 2D images to allow a smoother transition between the 2D images over time (e.g., a time lapse series) 161.

In some cases only a single 2D image is used, and compared with the 3D digital model, in which case the 2D image may be compared to a projection from the 3D digital model having the same identified camera angle.

In general, the 2D images may be correlated with the time at which the images were taken. The longitudinal comparison may be organized as a time series showing the change in the dentition include in all or a portion of the 2D image(s) over time. The longitudinal comparison may therefore include a set of 2D images, which may be indexed by time. The longitudinal comparison may be output (e.g., may be stored, transmitted, and/or displayed) 163.

Autocorrect Control

Figure 12A:
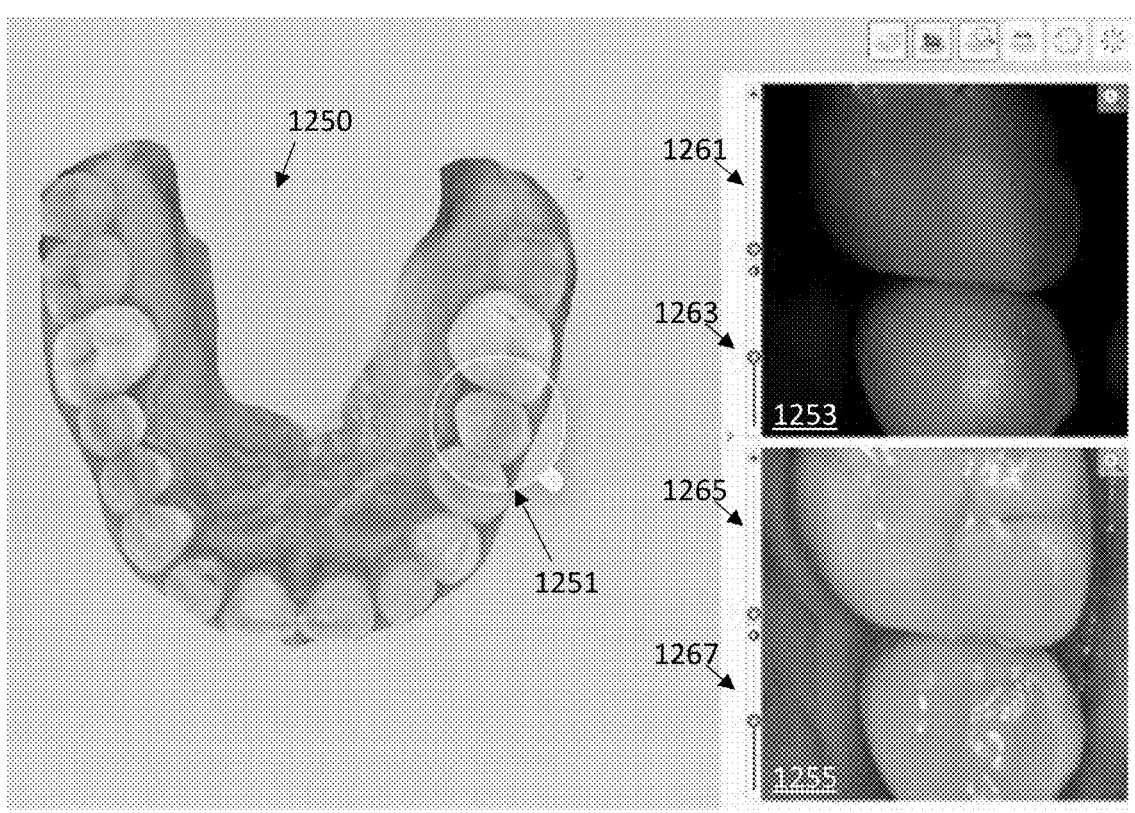
FIGS. 12A-12B show examples of images of imaging parameter control across multiple images.
Figure 12B:
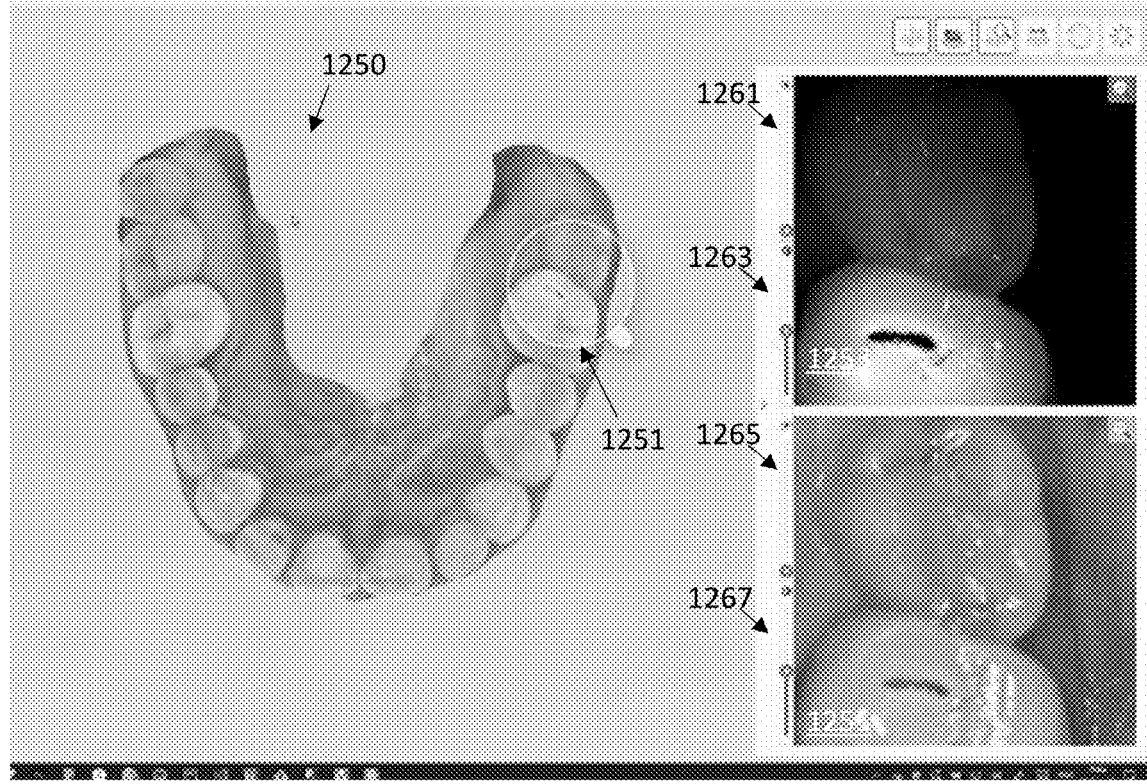

As mentioned above, any of the methods and apparatuses described herein may include an autocorrect control for controlling one or more imaging parameter across different imaging modalities and/or times in an optimized manner, using a single automated control. For example, currently, multiple tools (e.g., "sliders") are required to control and/or enhance the image quality for the near-IR and color images. For example, a separate brightness slider and contrast slider may be used for each image. Since many NIRI images are often much darker, and color images may also require improvements/modifications, the sliders need to be used often, and this not user friendly. FIGS. 12A-12B illustrate an example of a user interface including a display of a 3D model of a dental arch 1250 for an entire dental arch, which may be based on one or more intraoral scans. The user interface shown in FIGS. 12A and 12B also includes a viewing selector 1251 (shown as a window, shown as a loop; however any shape or structure may be used, including unbounded structures, e.g., a pointer). A pair of corresponding images 1253, 1255 are shown on the right, illustrating a near-IF 1253 and color 1255 image corresponding to the tooth region that the user has selected by controlling the position of the viewing selector. The orientation of either the viewing selector (e.g., the pseudo camera position looking at the teeth of the arch) and/or the 3D model of the arch may be moved relative to each other to allow other viewing perspectives, such as more buccal, lingual, anterior, posterior, etc., to be shown.

In this example ach of the two images 1253, 1255 shown on the right includes a pair of controls 1261, 1263, 1265, 1267 that are configured to independently control the brightness of the near-IR image 1261, the contrast of the near-IR image 1263, the brightness of the visible light image 1265, or the contrast of the visible light image 1267. As shown in FIG. 12B, relative movement between the virtual camera (e.g., the display selector 1251 in FIGS. 12A-12B) and the 3D model of the dental arch changes the images shown, but may not automatically adjust the contrast. Further, each of the different imaging modalities, near-IR and visible light.

Figure 13A:
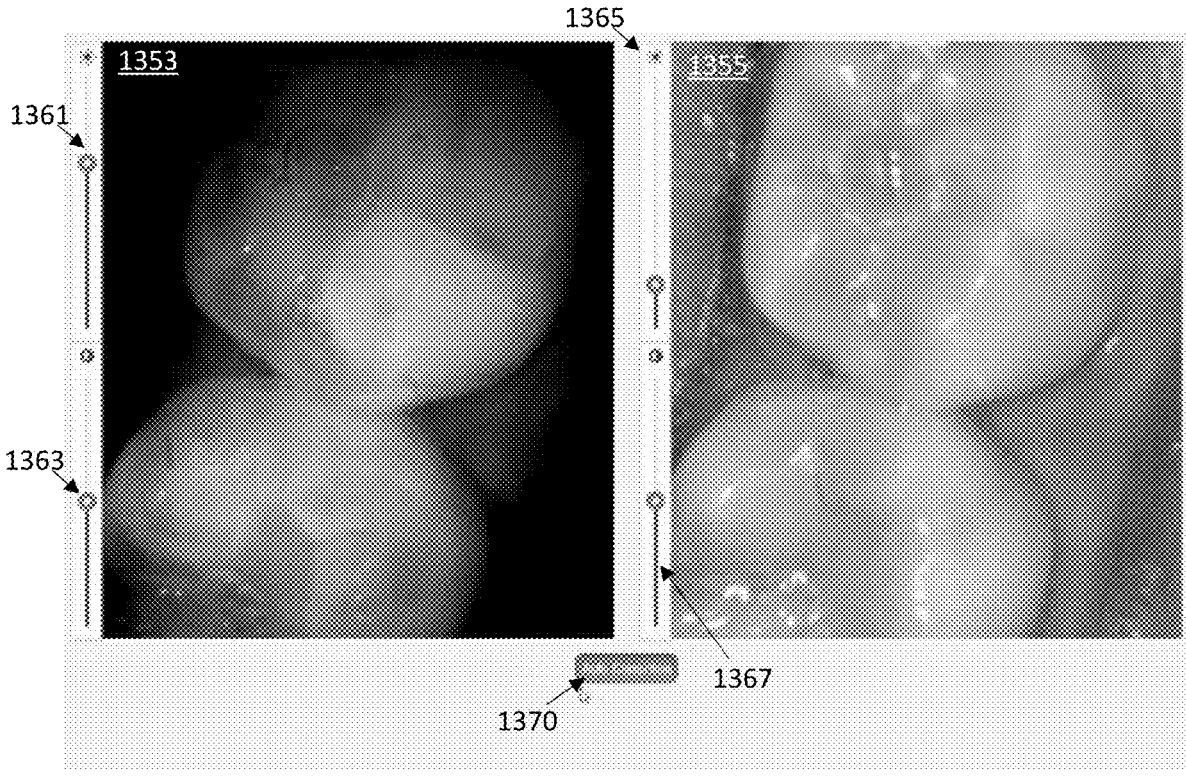
FIGS. 13A-13B show examples of images of imaging parameter control across multiple images.
Figure 13B:
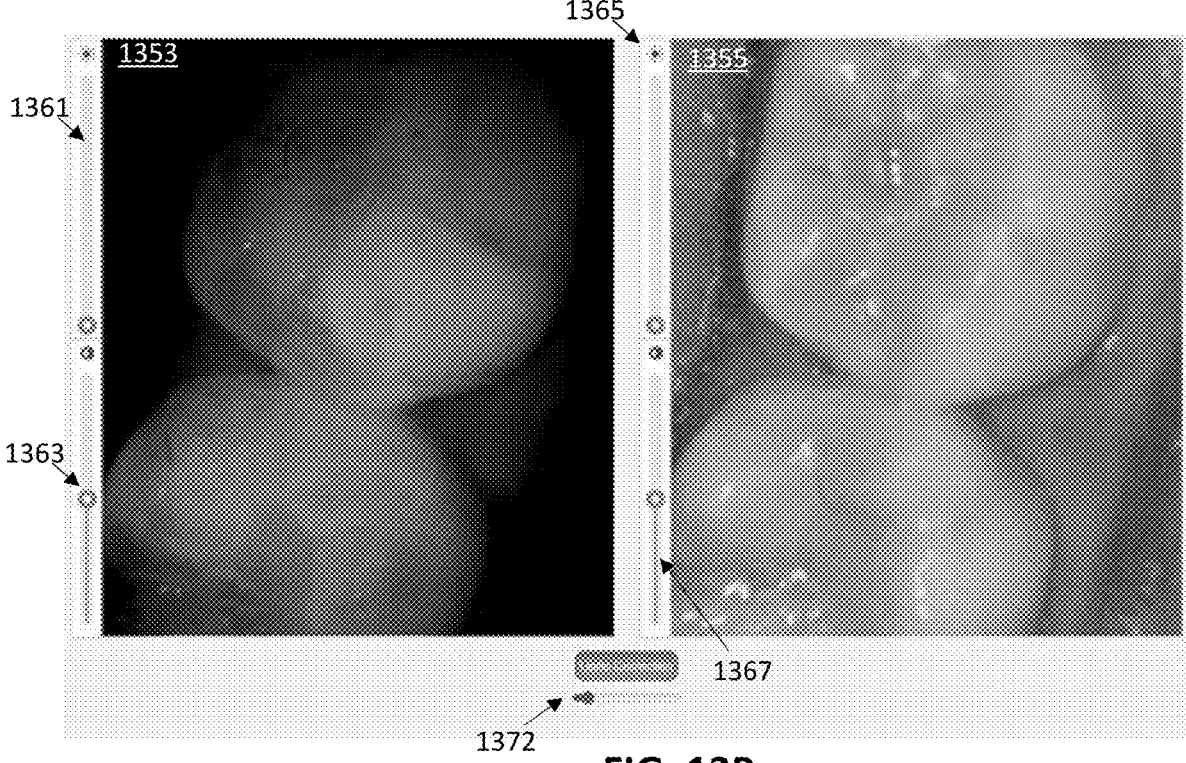

In some cases it may be best to either replace these multiple controls (e.g., 4 sliders in FIGS. 12A-12B) with just one control. Moreover, it would be very beneficial to automate the process between images of different modalities so that the different imaging parameters (e.g., brightness contrast, etc.). For example, the methods and apparatuses described herein may use an image auto-correction calculation to provide a single control (e.g., master control, such as a button, slider, etc.) that goes from zero correction to somewhat over-correction, and that permits the user to control (and, by default to automatically select a position that will permit optimal image correction level), so that in most images user will not need to adjust the correction at all. In some, as shown in FIGS. 13A-13B, the use of master control may be optionally toggled on/off using a toggle (shown as a button 1370). In FIG. 13A the display shows a near-IR image on the left 1353 and a corresponding visible light image on the right 1355. As in FIGS. 12A-12B each image may include separate imaging parameter controls; in this case, brightness 1361, 1365 and contrast 1363, 1367. By selecting the autocorrection toggle control 1370, a new, master control (slider 1372) may be provided as part of the user interface, allowing, by control of a single toggle, the user to select autocorrection (e.g., percent autocorrection) for all of the images displayed. In some cases the master control may include one or more (two or more, three or more, etc.) pre-set positions corresponding to, e.g., 0% autocorrect, 50% autocorrect, 100% autocorrect, etc.

Figures 14A, 14B:
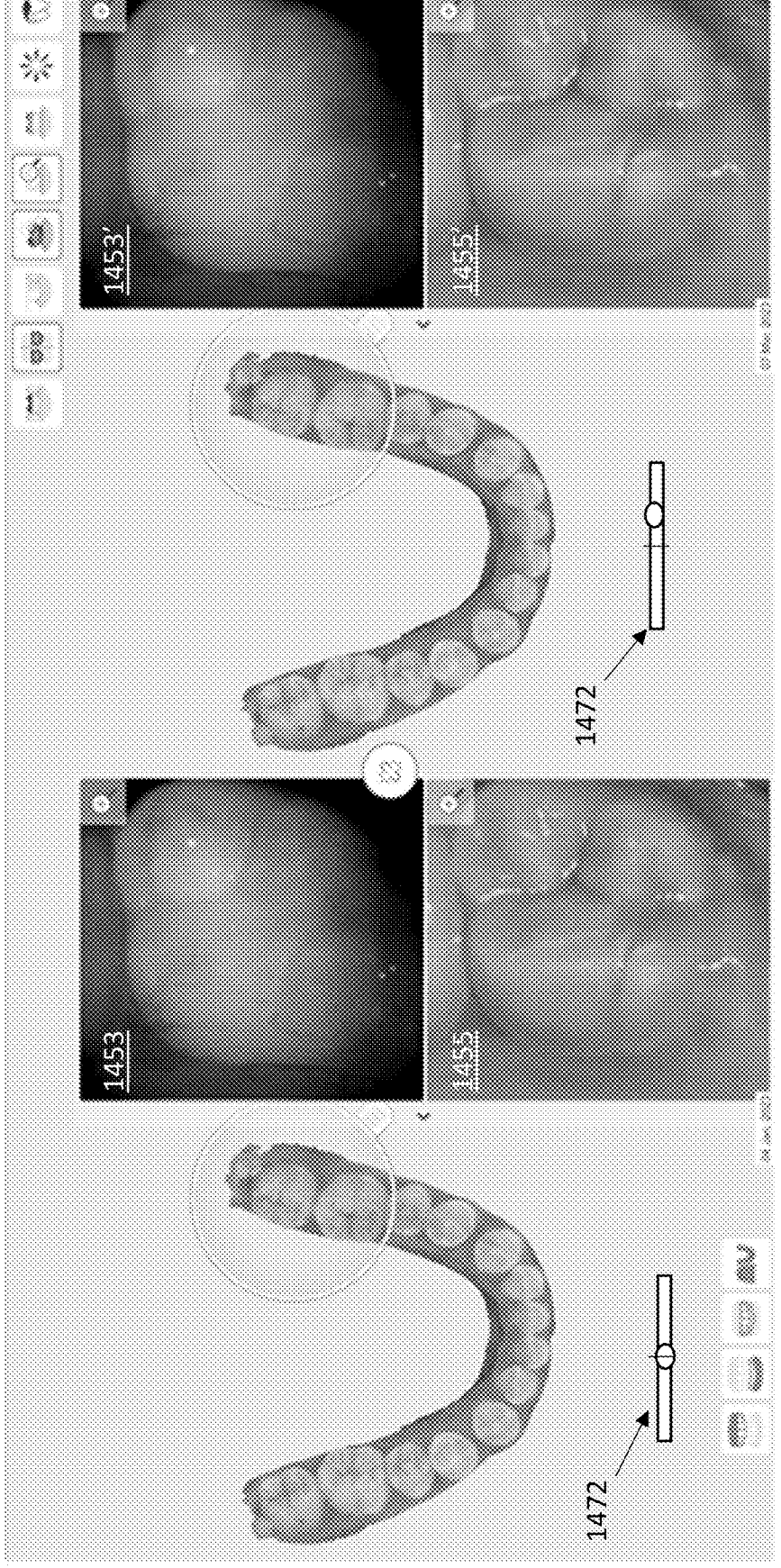
FIGS. 14A-14B show examples of images of imaging parameter control across multiple images.

FIGS. 14A-14B illustrates an examples in which a master controller (slider 1472) may be used to automatically control multiple imaging parameters with a single control. In FIG. 14A the autocorrect controller is shown in the neutral position (e.g., with 100% autocorrection) while FIG. 14B shows the master controller moved slightly to the right, increasing the percentage of autocorrect for both the near-IR 1453, 1453' and visible light images 1455, 1455' shown slightly overcorrected in FIGS. 14A and 14B. In this example the individual controls for the image parameters are not shown, however it should be understood that other controls may be used.

Figure 15:
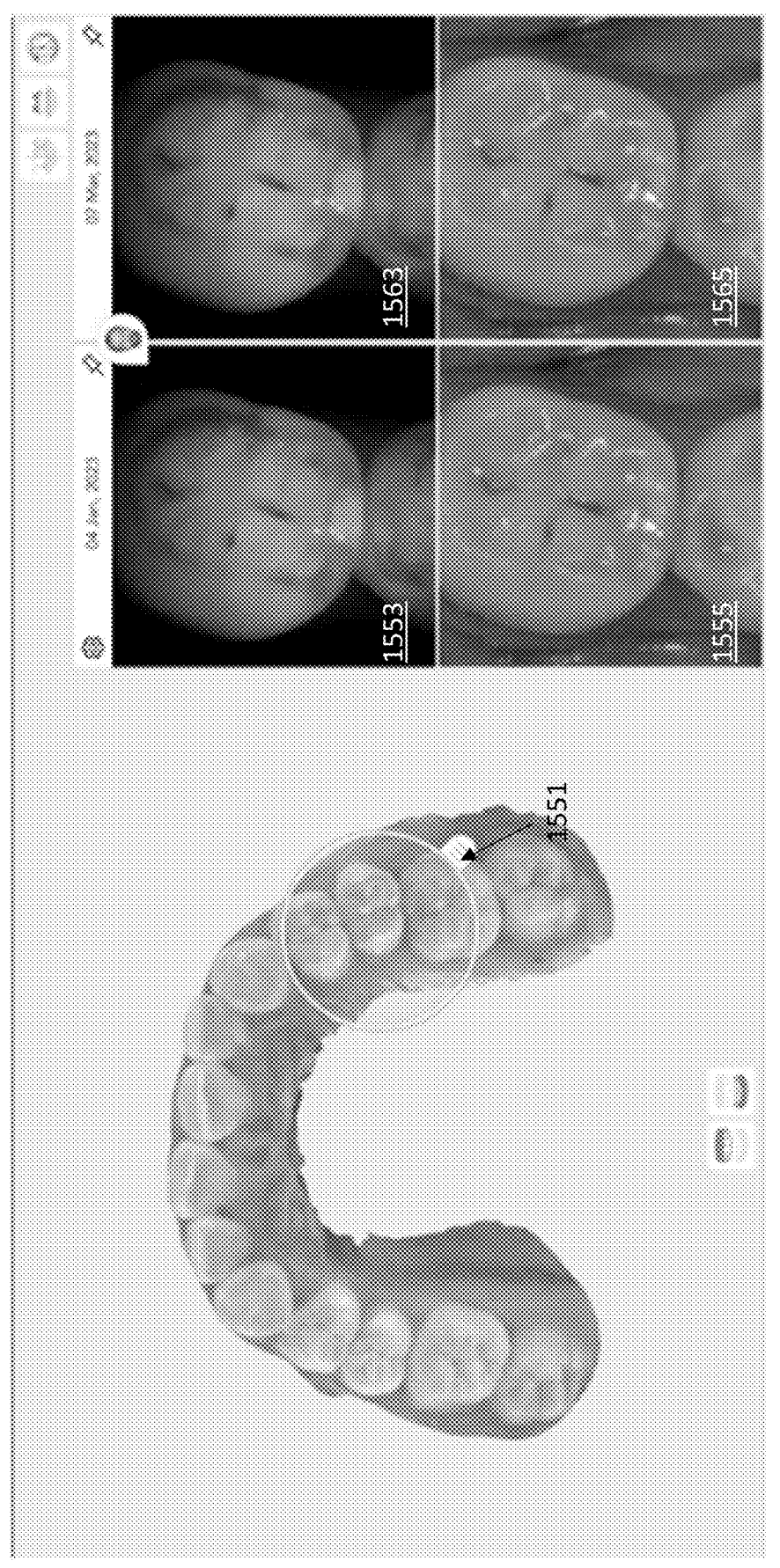
FIG. 15 illustrates one example of a user interface including a display showing representative images at different time, having imaging parameters controlled by a master controller as described herein.

The methods and apparatuses described herein for auto-correcting multiple related images may be used with any number of images, not limited to two. For example, in addition to different images corresponding to the same region of the teeth taken with different imaging modalities, these methods and apparatuses may be configured to be operated with longitudinal images, taken of the same tooth region(s) at different times, as described above. FIG. 15 shows an example of this. In FIG. 15, the image shows four images corresponding to the selected 1551, including a near-IR image of the region taken at a first time 1553, and a corresponding visible light image 1555 as well as a near-IR image of the region taken at a second time 1563, and a corresponding visible light image 1565. A master control may be used to simultaneously allow equivalent adjustment to autocorrect all four images.

Returning now to FIG. 11, FIG. 11 schematically illustrates one example of a method of simultaneously autocorrected and adjusting the correction (autocorrection) of a plurality of different images taken of a region of teeth, e.g., at different times, different imaging modalities, etc. The method may include receiving or accessing an intraoral scan of the patient's teeth, such as accessing an intraoral scan of a first image of a first region of an intraoral scan of a subject's teeth. The first image may preferably be taken using a first imaging modality, and the first image may have a first plurality of imaging parameters. These imaging parameters may be, e.g., contrast, and/or brightness. The imaging parameters corresponding to the image may be uncorrected or previously corrected 1101. The method may also include receiving or accessing a second image (or additional images) of the first region of the intraoral scan of the subject's teeth. The second (or more) images may be taken using a second (or more) imaging modality, and each may have a set of imaging parameters. The imaging parameters may be initially uncorrected or previously corrected.

The method may include autocorrecting the first image using one or more autocorrection modules to generate a first set of corrected imaging parameters 1103. For example, autocorrecting each image of the plurality of images independently using one or more autocorrection modules to generate, for each image of the plurality of images, a corresponding set of corrected imaging parameters. In some cases, the method may include autocorrecting the second image using the one or more autocorrection modules to generate a second set of corrected parameters.

The method may further include providing a master control input having a first uncorrected position, a second autocorrected position and a third overcorrected position, wherein the second autocorrected position is between the first uncorrected position and the third overcorrected position 1107. The method (or apparatus performing the method) may then receive a user-selected value from the master control input that is between the first and third positions 1109. For example, the user may input the value from a slider, knob, etc. The input value may be used to determine imaging parameters, e.g., by scaling the first plurality of uncorrected imaging parameters relative to the first set of corrected imaging parameters based on the user-selected value from the master control input 1111. The first image may then be displayed using the first plurality of display imaging parameters that were determined in this manner, and the second image may also be displayed using a second plurality of display imaging parameters that are determined by scaling the second plurality of uncorrected imaging parameters relative to the second set of corrected imaging parameters based on the user-selected value from the master control input 1113.

The methods and apparatuses for automatically modifying the optical parameters of a plurality of different images may provide a significant improvement in the user experience. In general, the automatic image correction (or semi-automatic, with limited user input to activate/modify the activity) may reduce the multi-parameter control of adjusting imaging parameters, such as contrast, brightness, color balance, etc., into a single parameter, which may be input from the master control. These techniques may be particularly useful in the context of an intraoral scanner, particularly one that provides multiple imaging modes, such as visible light, near-IR light, etc. For example, an intraoral scanner configured to include the automatic image correction (or semi-automatic image correction) may be configured to perform the correction calculation for NIRI and Color images in as part of the review tools.

For example, the methods and apparatuses described herein may be configured to optimize brightness and contrast for near-IR images to overcome dark areas and high return metallic objects, and natural color correction for color images. In some examples an automated agent (e.g., a machine learning agent) may, based on labeling tools usage, calculate a set of best image enhancements in order to provide the user with a single (e.g., "master") control that may be adjusted between positions including "no correction" to "over correction" in order to achieve an optimal view. As described herein, these techniques may include mapping the corrections, which may be based on multiple parameters, to a single controlling parameter. As described in FIGS. 12A-12B, multiple controls (e.g., in each of FIGS. 12A-12B individual sliders for each imaging parameter, contrast and brightness, are shown), which may individually control and enhance the image quality for the shown near-IR and color images. During routine operation, e.g., collecting images using an intraoral scanner, many near-IR images may be too dark and/or may be non-uniform; color images may also require improvements. Thus the need to use each of the multiple sliders may be cumbersome. The use of the master controller may alleviate this issue, but it is technically challenging to automatically coordinate each of the different imaging parameters using a single, one-dimensional value (e.g., percent correction) provided by the master controller. The use of a master control input may still enable the user to explore the image and get to a better understanding of what is visible in the images and permit the user to see the original image with no correction. As shown in FIGS. 13A-13B, the apparatuses and methods described herein may be configured to allow the user to toggle between the use of the master control (automatic/semi-automatic) adjustment and individual control.

In one example, the methods and apparatuses described herein may be used for longitudinal analysis, e.g., in which there are two or more images (scans) taken at different times that may be shown and concurrently adjusted (as shown in FIG. 15). For example, two, two-dimensional (2D) near-IR image and corresponding light images may be compared from two different intraoral scans (e.g., taken at different times). In this case, there may be two scans and therefore 4 images and 8 or more individual sliders; a master control may provide automatic/semi-automatic adjustment that is easy and may rapidly allow the user to see the best image quickly. Using the techniques described herein, the methods and apparatuses may reduce the multiple control (e.g., slider) to a single control (e.g., slider) per scan or even single slider for both scans (e.g., all four, or more, images).

Optionally, any of the methods and apparatuses described herein may include a memory that stores imaging parameter information, including but not limited to prior positions of the individual and/or master control(s). For example if a user moved a control such as a slider from a default correction to, e.g., half correction, when user drags the viewing selector to a different region (having correspondingly different images), the apparatus/method may keep the control at (for example) half correction and apply correction accordingly. In some cases the software may remember control setting per image for future use. For example, when re-opening the same scan or scan to review in the future.

In operation, the autocorrection techniques described herein may calculate for each 2D image the enhancement, separately for the different imaging modes (e.g., near-IR and color), that may be the default correction. In some examples the control (e.g., master control) default position may be in the center and may correspond to the default correction. The user may be able to move the control (e.g., slider) to a lowest (e.g., bottom) value, in order to get images with little or no correction (e.g., original images). The user may also move the control to a highest (e.g., top) value, to get the images with over-correction.

When moving the imaging region (e.g., window) to view another position on the 3D model, and getting another 2D images, the slider relative position will be kept, and new images will be shown accordingly.

In some examples the technique used by the methods and apparatuses described herein may be based on adding gain and offset to the image. For example, the original image may have an initial gain (gain0) of 1 and an initial offset (offset0) of 0, and the calculated corrected image may have a calculated gain (gainC) of 2 and a calculated offset (offset) of 20. Thus, the master control (e.g., slider) may move from position 0 (uncorrected) to position 2 (overcorrected), having a default position at position 1. For any arbitrary control position between positions 0 and 2, the control may be moved to a position x, in which the new position gain (gainX) and new position offset (offset) are equal to:

$$gainX = gain0 * (1 - X) + gainC * X \qquad [1]$$

$$offsetX = offset0(1 - X) + offsetC * X \qquad [2]$$

In some examples, the master controller may use a correction technique, and may adjust the images. For example, the original images (Img0) may be autocorrected to a corrected image (ImgC); as the control is adjusted by the user (e.g., moved from position 0 to position 2, where a default position at 1 is between these), to any arbitrary position, x, each image may be adjusted, e.g., by pixel calculation to $$ImgX = Img0 * (1 - X) + ImgC * X \qquad [3]$$

For example, when comparing two data sets (e.g., each with near-IR and color images), and/or when comparing across different data sets (e.g., longitudinally), the apparatus or method may receive images, e.g., near-IR images taken at different times, angles and lighting, and possibly by different wands. This may cause images to be of different quality, where simple auto correction may not bring similar looking results. To make the comparison easier, these methods and apparatuses may perform a mutual-image correction. For example, using any correction technique, the two (or more) images provided for the same location, the method and apparatus may generate similarly corrected images. For example, if the correction technique (e.g., correction algorithm) is based on gain and offset, the system/method may try to provide a gain and offset for each image that will equalize their histograms (so that the resulting histograms of the multiple different images or types of images will be similar).

In general, a variety of different correction techniques may be applied, including known correction techniques. For example, multiple ways to calculate autocorrection for images may be used as part of the methods and apparatuses described herein. Examples of appropriate correction algorithms may include: Automatic adjustment of Brightness and Contrast (see, e.g., https://stackoverflow.com/questions/37986669/auto-adjust-brightness-contrast-to-read-text-from-images, last visited Oct. 1, 2023), Automatic Histogram Warping algorithms (see, e.g., http://www.cycmaginary.com/Rendering/AutomaticHistogramWarping.pdf, last visited Oct. 1, 2023), adaptive gamma correction (see, e.g., https://arxiv.org/abs/11109.04427, last visited Oct. 1, 2023), intensity histograms (e.g., https://github.com/python-pillow/Pillow/blob/main/src/PIL/ImageOps.py, last visited Oct. 1, 2023), etc. These techniques may be integrated with the methods described herein to automatically and easily use a single user input to adjust multiple correction levels.

All publications and patent applications mentioned in this specification are herein incorporated by reference in their entirety to the same extent as if each individual publication or patent application was specifically and individually indicated to be incorporated by reference. Furthermore, it should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

When a feature or element is herein referred to as being "on" another feature or element, it can be directly on the other feature or element, or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under", or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intraoral scanning system, the system comprising:
a hand-held imaging sensor; and
a non-transitory, computer-readable storage medium comprising instructions which, when executed by a computer, cause the computer to carry out the steps of:
identifying a region of interest (ROI) on a first three-dimensional (3D) model of a patient's teeth derived from a first set of intraoral scan data taken over a first time period;
generating or selecting a first representative image that includes the ROI from a plurality of images corresponding to the first set of intraoral scan data;
mapping the ROI from the first 3D model to a second 3D model derived from a second set of intraoral scan data taken over a second time period;
generating a second representative image corresponding to the second 3D model, wherein the second representative image corresponds to a same camera angle relative to the second 3D model as the first representative image relative to the first 3D model and includes a region of the second 3D model that corresponds to the ROI; and
displaying the first and second representative images.

2. The system of claim 1, wherein generating or selecting the first representative image comprises selecting the first representative image from the plurality of images, and further wherein the selection is based on a number of points defining the ROI and/or a camera angle relative to a surface containing the ROI.

3. The system of claim 1, wherein generating or selecting comprises selecting based on how close a camera angle relative to a surface containing the ROI is to an angle normal to the surface containing the ROI.

4. The system of claim 1, wherein identifying the ROI comprises using a trained neural network to select the ROI, wherein the trained neural network is trained to identify one or more clinical features from the first 3D model or the plurality of images corresponding to the first set of intraoral scan data.

5. The system of claim 1, wherein identifying the ROI comprises receiving a manually identified ROI from a user.

6. The system of claim 1, further comprising finding correspondence between the first 3D model and the second 3D model of the patient's teeth, before generating the second representative image.

7. The system of claim 1, wherein identifying the ROI on the first 3D model comprises identifying the ROI in the plurality of images corresponding to the first set of intraoral scan data by identifying points corresponding to one or more of a plurality of points defining the ROI in each of the plurality of images corresponding to the first set of intraoral scan data, further wherein generating or selecting the first representative image comprises selecting the first representative image from the first plurality of images corresponding to the first set of intraoral scan data.

8. The system of claim 1, wherein identifying the ROI on the first 3D model comprises identifying the ROI in the plurality of images corresponding to the first 3D model by identifying points corresponding to one or more of a plurality of points defining the ROI in each of the plurality of images corresponding to the first set of intraoral scan data, further wherein generating or selecting the first representative image comprises generating a synthetic image from the first 3D model and/or the plurality of images corresponding to the first set of intraoral scan data.

9. The system of claim 8, wherein an angle normal to a surface containing the ROI is factored into a camera angle of the synthetic image that is generated.

10. The system of claim 1, further comprising identifying, in a plurality of images corresponding to the second set of intraoral scan data, points corresponding to one or more of a plurality of points defining the ROI on the first 3D model.

11. The system of claim 1, wherein generating the second representative image corresponding to the second 3D model comprises generating a synthetic image using the same camera angle relative to the second 3D model as the first representative image.

12. The system of claim 11, wherein generating the synthetic image comprises using a trained neural network to generate the synthetic image.

13. The system of claim 11, wherein generating the synthetic image further comprises textural mapping the synthetic image.

14. The system of claim 11, wherein generating the synthetic image further comprises generating the synthetic image by one or more of: light field fusion (LLFF), Neural Radiance Fields (NERF), or scene representation networks (SRN).

15. The system of claim 1, wherein the instructions are further configured to cause the computer to carry out an additional step of modifying the first and/or second representative images so that the first and second representative images match more closely to each other.

16. The system of claim 15, wherein modifying the first and/or second representative images comprises adjusting one or more of: perspective, rotation, brightness, contrast, resolution, or color equalization.

17. The system of claim 1, wherein displaying the first and second representative images comprises displaying the first and second representative images side-by-side.

18. The system of claim 1, wherein displaying the first and second representative images comprises displaying the first and second representative images as part of a video loop.

19. The system of claim 1, further comprising comparing the first and second representative images and outputting data regarding differences between the representative images.

20. The system of claim 19, wherein comparing comprises comparing a caries detection severity map for the first representative image to a caries detection severity map for the second representative image.

21. The system of claim 1, wherein the first set of intraoral scan data of the patient's teeth comprises infrared images.

22. An intraoral scanning system, the system comprising:
an imaging sensor; and
a non-transitory, computer-readable storage medium comprising instructions which, when executed by a computer, cause the computer to carry out the steps of:
identifying a plurality of points defining a region of interest (ROI) on a first three-dimensional (3D) model of a patient's teeth derived from a first intraoral scan taken over a first time;
finding correspondence between the first 3D model and a second 3D model of the patient's teeth derived from a second intraoral scan taken over a second time;
finding points corresponding to the plurality of points defining the ROI in each of a plurality of images corresponding to the first 3D model, and generating a first representative image, wherein the first representative image includes a maximum of the plurality of points defining the ROI and/or has a corresponding camera angle that is approximately normal to a surface containing the ROI in the 3D model;
generating a second representative image corresponding to the second 3D model, wherein the second representative image has a same camera angle as the first representative image relative to the second 3D model as the first representative image and includes a region of the second 3D model that corresponds to the ROI;
modifying the first and/or second representative images to adjust one or more of: perspective, rotation or color equalization so that the first and second representative images match more closely to each other; and
displaying the first and second representative images.

23. A non-transitory computer-readable medium comprising instructions which, when executed by one or more processors, causes the one or more processors to perform a method comprising:
identifying a region of interest (ROI) on a first three-dimensional (3D) model of a patient's teeth derived from a first set of intraoral scan data taken over a first time;
mapping the ROI in a plurality of images corresponding to the first 3D model of the first set of intraoral scan data;
generating or selecting a first representative image that includes the ROI from a plurality of images corresponding to the first set of intraoral scan data;
generating a second representative image corresponding to a second 3D model, wherein the second representative image corresponds to a same camera angle relative to the second 3D model as the first representative image and includes a region of the second 3D model that corresponds to the ROI;
modifying the first and/or second representative images so that the first and second representative images match more closely to each other; and
displaying the first and second representative images.

* * * * *